United States Patent [19]

Beard et al.

[11] 4,072,696
[45] Feb. 7, 1978

[54] 5(6)-BENZENE RING SUBSTITUTED BENZIMIDAZOLE-2-CARBAMATE DERIVATIVES HAVING ANTHELMINTIC ACTIVITY

[75] Inventors: Colin C. Beard, Palo Alto; John A. Edwards, Los Altos; John H. Fried, Palo Alto, all of Calif.

[73] Assignee: Syntex (U.S.A.) Inc., Palo Alto, Calif.

[21] Appl. No.: 434,656

[22] Filed: Jan. 18, 1974

Related U.S. Application Data

[63] Continuation-in-part of Ser. No. 331,852, Feb. 12, 1973, abandoned.

[51] Int. Cl.$^2$ .................. C07C 147/00; C07C 147/06; C07C 149/40
[52] U.S. Cl. ................................. 260/397.6; 260/454; 560/13; 424/300; 424/302; 424/308; 424/309
[58] Field of Search ........................ 260/470, 397.6, 454

[56] References Cited

U.S. PATENT DOCUMENTS

| | | | |
|---|---|---|---|
| 3,711,504 | 1/1973 | Adams et al. | 260/470 |
| 3,745,187 | 7/1973 | Noguchi et al. | 260/470 |
| 3,760,076 | 9/1973 | Baranyovits et al. | 260/243 |
| 3,766,243 | 10/1973 | Widdig et al. | 260/470 |
| 3,780,089 | 12/1973 | Widdig et al. | 260/470 |
| 3,796,710 | 3/1974 | Barker et al. | 260/243 R |
| 3,810,992 | 5/1974 | Menn | 424/300 |

FOREIGN PATENT DOCUMENTS

| | | | |
|---|---|---|---|
| 1,211,041 | 11/1970 | United Kingdom | 260/470 |
| 1,214,415 | 12/1970 | United Kingdom | 260/470 |

*Primary Examiner*—Howard T. Mars
*Attorney, Agent, or Firm*—Gerard A. Blaufarb

[57] ABSTRACT

Carbalkoxythioureidobenzene derivatives represented by the following formula:

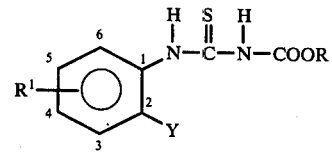

where R is a lower alkyl group having 1 to 4 carbon atoms; $R^1$ is $-SR^2$, $-SOR^2$, $-SO_2R^2$, $-OR^2$, $-SCN$, $-SC(O)NR^3R^4$, or $-M'(CH_2)_nMR^7$ where $n$ is 1-4; $R^2$ is lower alkyl having 1 to 6 carbon atoms, cycloalkyl having 3 to 7 carbon atoms, lower alkenyl or lower alkynyl having 3 to 6 carbon atoms, aralkyl or aryl, provided that when $R^1$ is $-SO_2R^2$, $R^2$ is not aralkyl or phenyl; $R^3$ and $R^4$ are independently hydrogen or lower alkyl having 1 to 6 carbon atoms; Y is amino, nitro, acylamino where the acyl portion has 1 to 6 carbon atoms, $-NHC(O)(CH_2)_mCOOH$ where $m$ is 1-6, or $-NHC(S)NHCOOR$; M and M' are independently O, S or

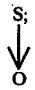

and $R^7$ is lower alkyl having 1 to 4 carbon atoms or aryl. The $R^1$ substitution is either at the 4- or 5-position.

The compounds are useful as pesticides, particularly as anthelmintic and antifungal agents.

51 Claims, No Drawings

5(6)-BENZENE RING SUBSTITUTED BENZIMIDAZOLE-2-CARBAMATE DERIVATIVES HAVING ANTHELMINTIC ACTIVITY

CROSS - REFERENCE TO PARENT APPLICATION

This application is a continuation-in-part application of application Ser. No. 331,852, filed Feb. 12, 1973 and now abandoned.

FIELD OF THE INVENTION

This invention relates to novel chemical compounds. More particularly, this invention relates to novel anthelmintically active carbalkoxythioureidobenzene derivatives wherein the benzene ring is additionally substituted at the 2- and 4-, or 2- and 5-position.

BACKGROUND OF THE INVENTION

Anthelmintically active 2-substituted carbalkoxythioureidobenzene derivatives either unsubstituted at the 4- or 5-position or substituted with different substituents than those described and claimed herein are known in this art (for example, see South African Pat. Nos. 70/08706, 71/03073, 71/03144, and 71/03924; and Japanese Pat. No. 71/22058).

SUMMARY OF THE INVENTION

The novel carbalkoxythioureidobenzene derivatives of the present invention can be represented by the following formula:

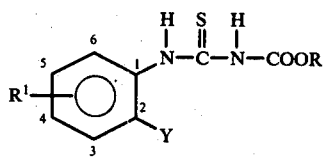

where $R$ is a lower alkyl group having 1 to 4 carbon atoms; $R^1$ is $-SR^2$, $-SOR^2$, $-SO_2R^2$, $-OR^2$, $-SCN$, $-SC(O)NR^3R^4$, or $-M'(CH_2)_nMR^7$ where $n$ is 1-4; $R^2$ is lower alkyl having 1 to 6 carbon atoms, cycloalkyl having 3 to 7 carbon atoms, lower alkenyl or lower alkynyl having 3 to 6 carbon atoms, aralkyl or aryl, provided that when $R^1$ is $-SO_2R^2$, $R^2$ is not aralkyl or phenyl; $R^3$ and $R^4$ are independently hydrogen or lower alkyl having 1 to 6 carbon atoms; Y is amino, nitro, acylamino where the acyl portion has 1 to 6 carbon atoms, $-NHC(O)(CH_2)_mCOOH$ where $m$ is 1-6, or $-NHC(S)NHCOOR$; M and M' are independently O, S or

and $R^7$ is lower alkyl having 1 to 4 carbon atoms or aryl. The $R^1$ substitution is either at the 4- or 5- position.

As used in this specification and claims, the term "lower alkyl" refers to both straight and branched chain alkyl groups having either a total of from 1 through 4 carbon atoms of from 1 through 6 carbon atoms, and thus includes primary, secondary and tertiary alkyl groups. Typical lower alkyls includes, for example, methyl, ethyl, n-propyl, isopropyl, n-butyl, isobutyl, t-butyl, n-amyl, n-hexyl and the like. The term "cycloalkyl" refers to cyclic hydrocarbon groups having from 3 to 7 carbon atoms. such as, for example, cyclopropyl, cyclopentyl, cyclohexyl, and the like. The term "lower alkenyl" refers to an unsaturated hydrocarbon group having from 3 to 6 carbon atoms and a single carbon-carbon double bond, provided that the double bond can not be on the α-carbon atom. Typical alkenyl groups include, for example, 2-propenyl, 2-butenyl, 3-butenyl, and the like. The term "lower alkynyl" refers to an unsaturated hydrocarbon group having from 3 to 6 carbon atoms, and a single carbon-carbon triple bond, provided also that the triple bond can not be on the α-carbon atom. Typical alkynyl groups include, for example, 2-propynyl, 2-butynyl, 3-butynyl, and the like. The alkyl, alkenyl or alkynyl group of the $R^2$ moiety can be optionally substituted with one or more radicals, for example, alkoxy, such as methoxy, aryl, such as phenyl, aroyl, such as benzoyl, hydroxy, cycloalkyl, halo, cyano or nitro radicals. The term "alkoxy" refers to the group having the formula RO- wherein R is a lower alkyl as defined above. Typical alkoxy groups include, for example, methoxy, ethoxy, t-butoxy and the like. The term "halo" refers to iodo, bromo, chloro and fluoro groups. The term "acyl" refers to acyl groups derived from carboxylic acids having from 1 through 6 carbon atoms such as acetyl, propionyl, butyryl, valeryl, isovaleryl, hexanoyl and the like. The term "aryl" refers to an aromatic hydrocarbon group, such as phenyl. The term "aralkyl" refers to an aryl substituted alkyl groups, such as for example, benzyl. The term "aroyl" refers to the group having the formula

where R' is an aryl or aralkyl group. The aryl or aralkyl groups can be optionally substituted with one or more lower alkyl, alkoxy, halo, nitro, cyano, thiocyanato, isothiocyanato, trifluoromethyl, alkylthio, alkylsulfinyl, alkylsulfonyl, acyl or acylamino where the acyl portion has 1 to 6 carbon atoms, $-SO_2NR^3R^4$ or $-N(R^3)SO_2R^4$ radicals; where $R^3$ and $R^4$ are independently hydrogen or lower alkyl having 1 to 6 carbon atoms. The term "succinamido" refers to the substituent represented by the formula

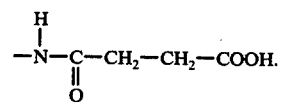

The compounds of the present invention, and the nontoxic salts thereof formed with pharmaceutically acceptable inorganic or organic acids, possess broad spectrum activity against parasites of mammals, including both mature and immature parasitic forms, as represented, for example, by the genera Trichostronglylus, Haemonchus, Ostertagia, Cooperia, Nematodirus, and Stronglyoides, and specifically, for example, against *Nematospiroides dubius, Hymenolepis Nana, Syphacia obvelata,* and/or *Aspiculuris tetraptera.* In particular, these compounds are found to exhibit high activity against various helminthic infections of the intestinal tract of economically important animals, coupled with low systemic toxicity to the host animal.

The compounds of the present invention are also useful as antifungal agents, particularly as systemic fungicides for controlling fungal diseases of plants of economic importance.

In addition to the stated anthelminthic and antifungal properties, certain compounds of the present invention are also useful as intermediates in the preparation of further compounds of this invention. For example, the 4- or 5-sulfinyl compounds can be prepared and then utilized as starting materials for the preparation of the corresponding 4- or 5-sulfonyl compounds.

Where Y is a basic moiety (eg, Y is amino), the term nontoxic salts as used herein refers to those pharmaceutically acceptable salts of the compounds of this invention which do not adversely affect the anthelmintic properties of the basic compound, such as those salts conventionally used in the pharmaceutical art. Such non-toxic salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like. Where the compound has an acidic moiety (eg, a carboxy group), the non-toxic salts thereof include the cation salts, such as, for example, the salts of sodiu, potassium, ammonium, and the like.

The amount of the compound to be administered will depend upon the actual compound utilized, and upon the weight of the animal being treated. In general, however, the daily dosage level will usually be between about 5 mg/kg and 100 mg/kg of body weight of the animal being treated. The active ingredient is adapted to be administered to the animal by mixing it with the diet of the animal, or formulating it with a non-toxic carrier to give anthelmitic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if the solid carrier is used, the compound can be administered in tablet or capsule form. If a liquid carrier is used, the medicament may be in the form of a soft gelatin capsule or in a liquid suspension.

In general, the compounds of the present invention can be prepared from a starting compound having nitro and amino or acylamino (for example, acetamido) substituents at the 1- and 2-positions, and the desired $R^1$ moiety (or a moiety which can be reacted to give the desired $R^1$ moiety) at the 4- or 5-position of the benzene ring. The nitro group is reduced to an amino group which is then reacted with an alkoxy carbonyl isothiocyanate to give the corresponding mono- or bis-carbalkoxythioureidobenzene derivative. When it is desired to retain the nitro group at the 2-position, the amino group is reacted with an alkoxy carbonyl isothiocyanate to give the corresponding carbalkoxythioureidobenzene derivative. Thereafter, the nitro group can be reduced to an amino group which, in turn, can be reacted to give, at the 2-position, an acylamino group. The 1,2-bis-carbalkoxythioureidobenzene derivatives are prepared from the corresponding 1,2-diamino compound by reaction with an appropriate amount of an alkoxy carbonyl isothiocyanate. The mono-carbalkoxythioureidobenzene derivative having a carboxyalkylcarbonylamino substituent at the 2-position can be prepared by reacting the compound where Y is amino with a cyclic acid anhydride, such as succinic anhydride.

The functional moiety at the 4- or 5- position can be, for example, the thiocyanato group which can be converted, by known reactions, to an alkylthio group. The functional group can also be halo which can be displaced to give an alkoxy, alkylthio, aryloxy or arylthio. The thio compounds can, in turn, be converted, also by known reactions, to the alkyl- or arylsulfinyl or alkylsulfonyl group. The functional moiety at the 4- or 5-position can also be hydroxy which can be converted to an alkoxy moiety, or it can be a phenoxy or substituted phenoxy group. In this regard, the thiocyanato, hydroxy, phenoxy, etc, starting materials are compounds previously reported in the literature.

A reaction sequence exemplifying these steps and adapted to produce various 4/5-alkylthio, arylthio, alkylsulfinyl, arylsulfinyl, and alkylsulfonyl mono- and bis-carbalkoxythioureidobenzene derivatives is as follows:

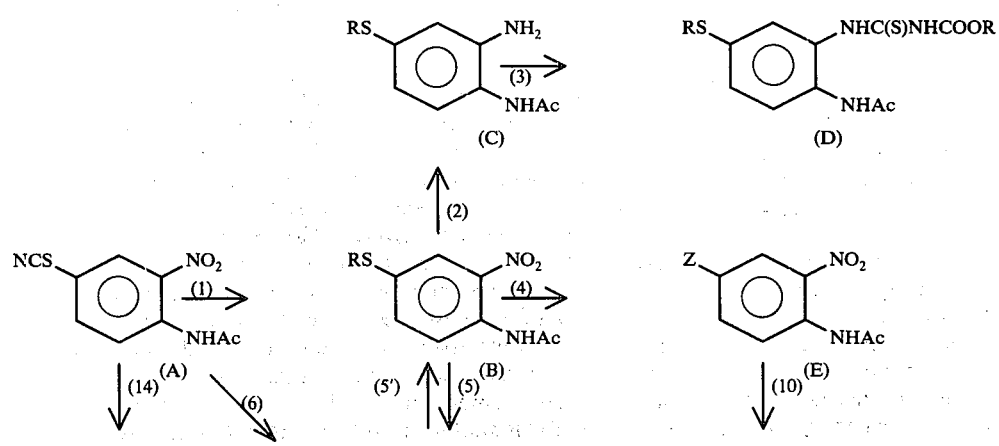

-continued

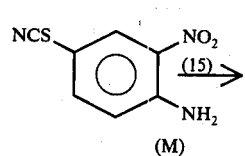
(M)

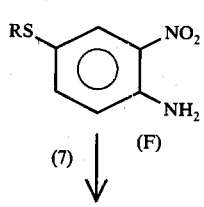
(F)

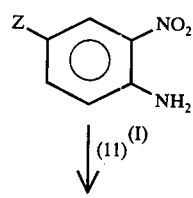
(I)

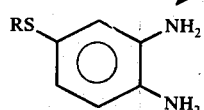

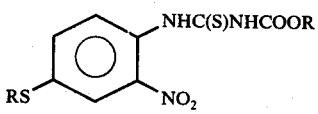
(G)

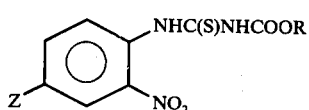
(J)

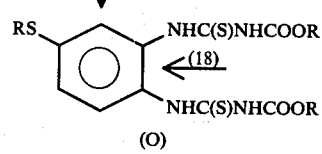
(O)

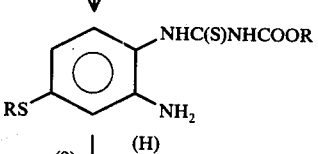
(H)

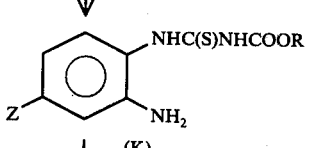
(K)

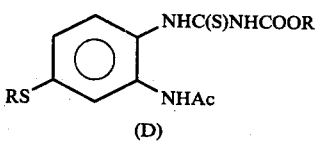
(D)

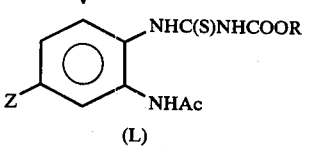
(L)

where Ac represents an acyl group, such as acetyl, and Z, depending upon the reactants and/or reaction conditions employed, represents

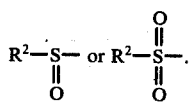

A suitable starting material is 1-acetamido-2-nitro-4-thiocyanatobenzene which can be prepared according to the method of F. Challenger and A. T. Peters, J. Chem. Soc., 1364 (1928). Other suitable starting materials include, for example, 1-amino-4-hydroxy-2-nitrobenzene, 1-acetamido-4-hydroxy-2-nitrobenzene, 1-acetamido-4-phenoxybenzene, 2-amino-4-chloro-1-nitrobenzene, and 2-acetamido-4-chloro-1-nitrobenzene.

Conversion of the thiocyanato group of the 1-acetamido-2-nitro-4-thiocyanatobenzene starting material to an alkylthio group, simultaneous with the conversion of the acetamido group to an amino group, as represented by step (6) above, can be effected by treating the thiocyanato compound (eg, compound A) with an alkylhalide or a cycloalkylhalide, in an alcoholic medium, such as methanol or ethanol, in the presence of base, such as potassium hydroxide, sodium hydroxide, potassium carbonate, or sodium carbonate. The reaction is conducted at a temperature from about 10° C to about 50° C, generally at about room temperature, for about ¼ to about 12 hours using essentially molar quantities of the halide reactant. Where the hydrocarbon radical of the halide reactant is dissimilar to the hydrocarbon radical of the alcoholic reaction medium, the reaction is preferably conducted in isopropanol or dimethylformamide. Optionally, the thiocyanato group can be converted to the alkylthio group, without change in the acetamido group, as exemplified by steps (1) and (15) above, by treatment of 1-acetamido-2-nitro-4-thiocyanato benzene or 1-amino-2-nitro-4-thiocyanatobenzene, at room temperature, with sodium borohydride in dimethylformamide, followed by treatment with the aforementioned halide reactant under the conditions as set forth above.

Reduction of the nitro group to an amino group, as exemplified by steps (2), (8), (12) and (16) above, can be effected by a variety of techniques. For example, the nitro group can be catalytically reduced utilizing hydrogen over a palladium/charcoal catalyst. This reaction is conducted in an inert solvent, such as methanol, at a temperature, for about ½ to about 2 hours. Other suitable inert solvents include ethyl acetate, acetic acid, and ethanol. This technique is particularly suitable for compounds which contain an alkoxy, phenoxy, sulfinyl or sulfonyl substituent at the 4- or 5-position.

Another suitable reducing technique is to treat the nitro-containing compound with iron powder and a ferrous salt, such as ferrous sulfate or ferrous chloride, in aqueous methanol at reflux under neutral conditions for about 1 to about 6 hours. Other suitable reaction media include acetic acid or concentrated hydrochloric acid, and other suitable salts include the corresponding zinc salts. It is desirable to add the iron powder in distinct portions (as opposed to all at one time), and to carefully monitor the reactants and reaction conditions to insure, for example, that sulfinyl compounds are not reduced to the corresponding thio compounds. This technique is suitable for starting materials which contain an alkoxy, phenoxy, sulfonyl, alkylthio or arylthio substituent.

A reduction technique suitable for use with alkoxy or aryloxy substituent-containing compounds, but particularly suitable for use with alkylthio and arylthio compounds, is to treat such compounds with stannous chloride in concentrated hydrochloric acid at a temperature in a range from about −20° C to about 100° C, generally about room temperature, for about ½ to 6 hours. An excess of the stannous chloride reactant should be utilized, generally about 5 parts (by weight) per unit weight of the nitro group-containing compound.

The conversion of the amino group to the carbalkoxythioureido substituent, as exemplified by steps (3), (7), (11) and (17) above, is achieved by reacting the amino group with an alkoxy carbonyl isothiocyanate, such as methoxy carbonyl isothiocyanate or ethoxy carbonyl isothiocyanate, in an inert reaction medium, such as acetone, tetrahydrofuran, dioxane, or dimethylformamide. This reaction is typically conducted at a temperature from about 0° C. to about 60° C., generally about room temperature, for about ¼ hour to about 120 hours using an excess of the isothiocyanate reactant, generally about a two-fold excess.

Conversion of the alkylthio or arylthio group to the corresponding sulfinyl or sulfonyl group, or conversion of the sulfinyl to the sulfonyl group, as exemplified by step (4), above, is conveniently effected by treatment with a peracid, such as peracetic acid, perbenzoic acid, metachloroperbenzoic acid, or perphthalic acid, in an inert solvent for the compound being treated. Suitable solvent materials include, for example, methylene chloride or chloroform. If the compound being treated is not soluble in the particular reaction media desired to be utilized, then a co-solvent material, such as acetic acid or methanol, should be utilized in an amount sufficient to dissolve the compound being treated. Typically, the reaction is conducted at a temperature from about −30° C to about room temperature for about ½ hour to about 6 hours. When it is desired to convert the alkylthio or phenylthio group to the sulfinyl group, molar quantities are utilized, and reaction conditions are carefully monitored to insure that the reaction does not proceed further than desired. When it is desired to convert the alkylthio group to the alkylsulfonyl group, or it is desired to convert the alkylsulfinyl group to the alkylsulfonyl group, an excess of the peracid material, for example, 2 moles of the peracid per mole of the compound being treated, is utilized and the reaction conditions do not have to be as carefully monitored. Optionally, such conversions can also be effected by treatment with periodate in aqueous methanol or aqueous acetonitrile at a temperature in the range of about −20° C. to about 50° C. for about ½ to about 12 hours.

Conversion of an acylamino group, for example, an acetamido group, to an amino group, as exemplified by steps (5), (10) and (14) above, can be effected by treating the acylamino group-containing compound with a strong acid or strong base, such as sodium hydroxide, potassium hydroxide, potassium carbonate, sodium carbonate, or hydrochloric acid, in aqueous methanol at about 20° C to about 100° C for about ¼ to about 24 hours. The selection of either the strong acid or the strong base will depend upon the substituent at the 4- or 5- position; for example, with the presence of an thiocyanato substituent, a strong acid must be utilized if that substituent is to be retained. Generally, for other substituents disclosed a strong base is utilized; however, the necessary material for a particular substituent or compound can be determined by routine experimentation or will be apparent from the nature and chemical stability of the particular compound involved.

The conversion of an amino group to an acylamino group, for example, an acetamido group, as exemplified by steps (5'), (9) and (13) above, can be conveniently effected by treatment with an acyl halide, for example acetyl chloride, in an inert organic reaction medium which dissolves, or is adjusted to dissolve, the compound being treated. For example, suitable organic reaction media include tetrahydrofuran in the presence of pyridine, acetone in the presence of base such as potassium hydroxide or potassium carbonate, or pyridine alone. Acetic anhydride can be used as the acylating reactant and can also be utilized as the reaction media. When so utilized, the acetic anhydride is present in substantial excess, generally in an amount sufficient to dissolve the compound being reacted. The well-known Schotten-Baumann reaction can also be utilized for the above purpose. In such a reaction, the compound being treated is dissolved in an aqueous base, an excess of acetic anhydride is added and the precipitated product collected by filtration. When acetic anhydride is utilized in these reactions, it can be utilized in combination with an acidic catalyst, such as sulfuric acid or paratoluene-sulfonic acid. These reactions are typically conducted at a temperature from about −30° C to about room temperature for about ¼ to about 24 hours using a slight excess (about 1.5–2 moles) of the acylating agent.

The nitro group of Compound E above can be reduced to an amino group which, in turn, can be reacted with an alkoxy carbonyl isothiocyanate, as set forth above with respect, e.g., to step (3), to give the corresponding 2-acylamino-1-carbalkoxythioureidobenzene compound. The amino containing compound can also have the acylamido group reduced to an amino group to give the 1,2-diamino compound which is reacted, as in step (17), with two molar equivalents of an alkoxy carbonyl isothiocyanate to give the corresponding 1,2-bis-carbalkoxythioureidobenzene compound. The 1,2-diamino compound can also be obtained by reducing the nitro group of compound I.

The mono-carbalkoxythioureidobenzene compound having an amino group at the 2-position can be reacted with a cyclic acid anhydride, such as succinic anhydride, to give the compounds of the present invention where Y is —NHC(O) $(CH_2)_m$COOH. This reaction can be effected in an inert solvent, such as tetrahydrofuran, at room temperature to about the reflux temperature of the solvent for about 1 to about 24 hours.

The thiocyanato group at the 4- or 5-position can be converted to a carbamoylthio group, by dissolving, for example, compound A in concentrated sulfuric acid at 0° C. for about 12 to about 24 hours, and then quenching the reaction mixture in ice water. This reaction is applicable, for example, to the preparation of 1-amino-4-carbamoylthio-2-nitrobenzene from 1-acetamido-2-nitro-4-thiocyanato benzene (i.e., compound A). The carbamoylthio compound so produced can have the nitro and-/or amino substituents thereof retained and/or converted to other substituents, via the reaction steps set forth above, to afford the corresponding 4- or 5-carbamoythio-1-mono or 1,2-bis-carbalkoxythioureidobenzene compounds of this invention.

When 2-amino-4-chloro-1-nitrobenzene or 2-acetamido-4-chloro-1-nitrobenzene is utilized as a starting material, it can be converted to the corresponding 4-alkylthio or 4-arylthio compound by the reaction thereof with an alkyl mercaptan or aryl mercaptan in an inert solvent, such as dimethylformamide, in the presence of a suitable inorganic base, such as sodium hydride, potassium carbonate or sodium carbonate. Typically, this reaction is conducted at a temperature from about 20° C. to about 150° C (ie, to about the reflux temperature of the solvent material) for about ½ to about 6 hours, using a slight excess (1.5–2 moles) of the mercaptan reactant. The 2-amino-4-chloro-1-nitrobenzene or 2-acetamido-4-chloro-1-nitrobenzene starting material can also be converted to the corresponding 4-arylsulfonyl compound by displacement of the chlorine with metal arylsulfinate, for example sodium phenylsulfinate. This displacement is typically conducted in an inert, polar organic solvent, such as dimethylformamide, acetone, or dimethylsulfoxide, at a temperature from about room temperature to the reflux temperature of the particular solvent employed for about ½ to about 6 hours, using essentially a molar ratio of the starting material and the metal sulfinate. The compounds so produced can be treated as set forth above to afford the mono- or bis-carbalkoxythioureidobenzene compounds of the present invention.

The 2-amino-4-chloro-1-nitrobenzene starting material can be converted to the corresponding alkoxy or aryloxy compound in accordance with the displacement procedure described above wherein the 4-chloro compound is reacted with an alkyl or aryl mercaptan, except that an alkanol or aryl alcohol is utilized in place of the mercaptan reactant and the reaction time is somewhat longer, generally on the order of about 1 to about 24 hours.

When 1-acetamido-4-hydroxy-2-nitrobenzene is utilized as the starting material, the hydroxy substituent can be converted to an alkoxy substituent by reaction of the starting material with an alkyl halide in an inert organic solvent, such as dimethylformamide or acetone, in the presence of a suitable organic base, for example, sodium hydroxide, potassium carbonate, etc. This reaction is typically conducted at a temperature from about room temperature to about the reflux temperature of the particular solvent material employed for about 1 to about 24 hours using about 1.5 to about 6 moles of the alkyl halide per mole of the starting material.

1-Acetamido-4-phenoxybenzene can be nitrated to 1-acetamido-2-nitro-4-phenoxybenzene by the techniques described by Scarborough, J. Chem. Soc. 132, 2361 (1929) or Oesterlin, Monatsh., 57, 31 (1931).

The 2-amino-4-alkoxy-1-nitrobenzene, 2-amino-4-aryloxy-1-nitrobenzene, 1-acetamido-4-alkoxy-2-nitrobenzene, and 1-acetamido-2-nitro-4-phenoxybenzene compounds so produced can also be treated as set forth above to afford the desired 4- or 5- alkoxy, aryloxy or phenoxy-1-mono- or 1,2-bis-carbalkoxythioureidobenzene compounds of the present invention. For example, the nitro group of 1-acetamido-2-nitro-4-phenoxybenzene can be reduced to an amino group, and then the amino group converted to the carbalkoxythioureido group to afford 2-acetamido-5-phenoxy-1-carbalkoxythioureidobenzene.

The thiocyanato group of an appropriate starting material (eg, 1-acetamido-2-nitro-4-thiocyanatobenzene) can be reacted with either an alkylthioalkylhalide or an alkoxyalkylhalide, to afford the corresponding alkylthioalkylthio- or alkoxyalkylthio- compound. This reaction can be conducted in an alcoholic medium, such as methanol or ethanol, in the presence of base, such as potassium hydroxide, sodium hydroxide, potassium carbonate or sodium carbonate, at a temperature from about 10° C. to about 50° C., generally at about room temperature, for about ¼ to about 12 hours using essentially molar ratios of the halide reactant and the thiocyanato starting material. As with the reaction exemplified by step (6) above, when the hydrocarbon radical of the halide reactant is dissimilar to the hydrocarbon radical of the alcoholic reaction medium, the reaction is preferably conducted in dimethylformamide.

The alkoxyalkoxy- or alkylthioalkoxy- derivatives are prepared by reacting a 4(5)-hydroxybenzene derivative (eg, 1-acetamido-4-hydroxy-2-nitrobenzene) with the alkylthio- or alkoxy-alkylhalide reactant referred to above. This reaction is also conducted in an inert organic solvent, such as dimethylformamide or acetone, in the presence of a base, such as potassium carbonate, etc., at a temperature from about room temperature to about the reflux temperature of the particular solvent material employed (eg, to about 150° C.) for about 1 to about 24 hours using a slight excess of the halide reactant.

The nitro group on compound F or I can be reduced under conditions set forth above to an amino group to give a 1,2-diamino compound. Such compounds can be reacted with an appropriate quantity of the alkoxy carbonyl isothiocyante reactant to give the corresponding 1,2-bis-carbalkoxythioureido compounds of this invention.

Compound M can be reacted with an alkoxy carbonyl isothiocyanate, under conditions as set forth above, to give the corresponding 1-carbalkoxythioureidobenzene compound having an ortho-nitro group. The nitro group can be reduced to an amino group, and, in turn, the amino group can be converted to an acylamino group, both steps being under conditions as set forth above.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the scope of the present invention but not particularly described in this specification, will be apparent to those skilled in this art.

In the above reaction sequence, where a carbalkoxythioureido substituent is first formed on the benzene nucleus, the substituent is placed at the 1-position to conform the formula representation of the compound produced to that given in the Summary of the Invention section above. This necessitates the simultaneous change of the position of other substituents on the benzene nucleus. A cursory examination of the mono- or bis- carbalkoxythioureido compound so produced and its immediate precursor will show, however, that the same relative positioning of all substituents has been retained.

Exemplary of the compounds of the present invention, as represented by the structural formula above, are the following illustrative compounds:

1,2-bis-(3-carbomethoxy-2-thioureido)-4-n-butylthiobenzene;
1,2-bis-(3-carbomethoxy-2-thioureido)-4-n-butoxybenzene;
1,2-bis-(3-carbomethoxy-2-thioureido)-4-methylsulfinylbenzene;
1,2-bis-(3-carbomethoxy-2-thioureido)-4-thiocyanatobenzene;
1,2-bis-(3-carbomethoxy-2-thioureido)-4-iso-propylsulfinylbenzene;
1,2-bis-(3-carbomethoxy-2-thioureido)-4-n-propylsulfinylbenzene;
1,2-bis-(3-carbomethoxy-2-thioureido)-4-n-butylsulfinylbenzene;
1,2-bis-(3-carbomethoxy-2-thioureido)-4-phenoxybenzene;
1,2-bis-(3-carbomethoxy-2-thioureido)-4-ethylsulfinylbenzene;
1,2-bis-(3-carbomethoxy-2-thioureido)-4-methoxymethoxybenzene;
1,2-bis-(3-carbomethoxy-2-thioureido)-4-ethoxymethoxybenzene;
1,2-bis-(3-carbomethoxy-2-thioureido)-4-methoxymethylthiobenzene;
1,2-bis-(3-carbomethoxy-2-thioureido)-4-p-chlorophenoxybenzene;
1,2-bis-(3-carbomethoxy-2-thioureido)-4-methylthiomethoxybenzene;
1,2-bis-(3-carbomethoxy-2-thioureido)-4-[1-(2-hydroxy-2-phenyl)-ethoxy] benzene;
2-acetamido-1-(3-carbomethoxy-2-thioreido)-5-methylthiobenzene;
2-acetamido-1-(3-carbomethoxy-2-thioureido)-5-ethylthiobenzene;
2-acetamido-1-(3-carbomethoxy-2-thioureido)-5-n-propylthiobenzene;
2-acetamido-1-(3-carbomethoxy-2-thioureido)-5-n-butylthiobenzene;
2-acetamido-1-(3-carbomethoxy-2-thioureido)-5-benzylthiobenzene; and
2-amino-1-(3-carbomethoxy-2-thioureido)-5-phenylthiobenzene. The aforementioned compounds are presently preferred because they have shown substantial activity against the helminths specifically referred to above.

Other illustrative compounds falling within the scope of the present invention include:
1,2-bis-(3-carbomethoxy-2-thioureido)-4-methoxybenzene;
1,2-bis-(3-carbomethoxy-2-thioureido)-4-methylsulfonylbenzene;
1,2-bis-(3-carbomethoxy-2-thioureido)-4-isopropylthiobenzene;
1,2-bis-(3-carbomethoxy-2-thioureido)-4-n-butylsulfonylbenzene;
1,2-bis-(3-carbomethoxy-2-thioureido)-4-n-amylsulfinylbenzene;
1,2-bis-(3-carbomethoxy-2-thioureido)-4-benzylsulfinylbenzene;
1,2-bis-(3-carbomethoxy-2-thioureido)-4-isobutylsulfinylbenzene;
1-(3-carbomethoxy-2-thioureido)-2-nitro-5-phenylsulfinylbenzene;
1,2-bis-(3-carbomethoxy-2-thioureido)-4-isoamylsulfinylbenzene;
1,2-bis-(3-carbomethoxy-2-thioureido)-4-phenylthiobenzene;
1,2-bis-(3-carbomethoxy-2-thioureido)-4-benzyloxybenzene;
1,2-bis-(3-carbomethoxy-2-thioureido)-4-methoxyethylsulfinylbenzene;
1,2-bis-(3-carbomethoxy-2-thioureido)-4-methoxyethoxybenzene;
1,2-bis-(3-carbomethoxy-2-thioureido)-4-p-methoxyphenoxybenzene;
1,2-bis-(3-carbomethoxy-2-thioureido)-4-phenylsulfinylbenzene;
1-(3-carbomethoxy-2-thioureido)-2-nitro-4-methylthiobenzene;
1-(3-carbomethoxy-2-thioueido)-2-nitro-4-methoxybenzene;
1-(3-carbomethoxy-2-thioureido)-2-nitro-4-thiocyanatobenzene;
1-(3-carbomethoxy-2-thioureido)-2-nitro-4-methylsulfonylbenzene;
1-(3-carbomethoxy-2-thioureido)-2-nitro-4-n-butylthiobenzene;
1-(3-carbomethoxy-2-thioureido)-2-nitro-4-phenoxybenzene;
2-acetamido-1-(3-carbomethoxy-2-thioureido)-5-methylsulfonylbenzene;
2-acetamido-1-(3-carbomethoxy-2-thioreido)-5-methylsulfinylbenzene;
2-acetamido-1-(3-carbomethoxy-2-thioureido)-5-n-butylsulfonylbenzene;
2-amino-1-(3-carbomethoxy-2-thioureido)-4(5)-phenylsulfinylbenzene;
2-acetamido-1-(3-carbomethoxy-2-thioureido)-4-methylthiobenzene;
2-acetamido-1-(3-carbomethoxy-2-thioureido)-4-n-butylthiobenzene;
2-acetamido-1-(3-carbomethoxy-2-thioreido)-5-n-butylsulfinylbenzene;
2-acetamido-1-(3-carbomethoxy-2-thioureido)-5-n-butoxybenzene;
2-acetamido-1-(3-carbomethoxy-2-thioureido)-5-phenylthiobenzene;
2-amino-1-(3-carbomethoxy-2-thioureido)-4-methylthiobenzene;
2-amino-1-(3-carbomethoxy-2-thioureido)-4-n-butylthiobenzene;
2-amino-1-(3-carbomethoxy-2-thioureido)-5-methylthiobenzene;
2-amino-1-(3-carbomethoxy-2-thioureido)-4-methylsulfinylbenzene;
1,2-bis-(3-carbethoxy-2-thioureido)-4-n-propylsulfinylbenzene;
1,2-bis-(3-carbethoxy-2-thioureido)-4-n-butylsulfinylbenzene;
1,2-bis-(3-carbopropoxy-2-thioureido)-4-n-propylsulfinylbenzene;
1,2-bis-(3-carbopropoxy-2-thioureido)-4-n-butylsulfinylbenzene;
1,2-bis-(3-carbobutoxy-2-thioureido)-4-n-propylsulfinylbenzene;
1,2-bis-(3-carbobutoxy-2-thioureido)-4-n-butylsulfinylbenzene;
2-acetamido-1-(3-carbethoxy-2-thioureido)-4-n-propylsulfinylbenzene;
2-acetamido-1-(3-carbopropoxy-2-thioureido)-4-n-butylsulfinylbenzene;
2-acetamido-1-(3-carbobutoxy-2-thioureido)-4-n-butylsulfinylbenzene;
2-acetamido-1-(3-carbomethoxy-2-thioureido)-5-allylthiobenzene;

2-acetamido-1-(3-carbomethoxy-2-thioureido)-5-[1-(3-chloro-2-hydroxy)-propoxy] benzene;
2-acetamido-1-(3-carbomethoxy-2-thioureido)-5-(2-hydroxy-2-phenylethoxy)benzene;
1,2-bis-(3-carbomethoxy-2-thioureido)-4-[1-(2-hydroxy-3-methoxy)-propoxy]benzene;
2-amino-1-(3-carbethoxy-2-thioureido)-4-n-propylsulfinylbenzene;
2-amino-1-(3-carbopropoxy-2-thioureido)-4-n-propylsulfinylbenzene;
2-amino-1-(3-carbobutoxy-2-thioureido)-4-n-butylsulfinylbenzene;
1-(3-carbethoxy-2-thioureido)2-nitro-4-n-propylsulfinylbenzene;
1-(3-carbethoxy-2-thioureido)-2-nitro-4-n-butylsulfinylbenzene;
1-(3-carbopropoxy-2-thioureido)-2-nitro-4-n-propylsulfinylbenzene;
1-(3-carbobutoxy-2-thioureido)-2-nitro-4-n-butylsulfinylbenzene;
1-(3-carbomethoxy-2-thioureido)-2-(3-carboxypropion-1-ylamido)-4-n-propylsulfinylbenzene;
1-(3-carbomethoxy-2-thioureido)-2-(3-carboxypropion-1-ylamido)-4-n-butylsulfinylbenzene;
1-(3-carbomethoxy-2-thioureido)-2-(3-carboxypropion-1-ylamido)-5-n-propylsulfinylbenzene;
1-(3-carbomethoxy-2-thioureido)-2-(3-carboxypropion-1-ylamido)-5-n-butylsulfinylbenzene;
1-(3-carbomethoxy-2-thioureido)-2-(4-carboxybutyr-1-ylamido)-4-n-propylsulfinylbenzene; and 2-amino-1-(3-methoxycarbonyl-2-thioureido)-4-phenoxybenzene;
2-amino-1-(3-methoxycarbonyl-2-thioureido)-5-phenoxybenzene;
2-amino-1-(3-methoxycarbonyl-2-thioureido)-4-(4-chlorophenoxy)benzene;
2-amino-1-(3-methoxycarbonyl-2-thioureido)-5-(4-chlorophenoxy(benzene;
2-amino-1-(3-methoxycarbonyl-2-thioureido)-4-(4-fluorophenoxy)benzene;
2-amino-1-(3-methoxycarbonyl-2-thioureido)-5-(4-fluorophenoxy)benzene;
2-amino-1-(3-methoxycarbonyl-2-thioureido)-4-(3-fluorophenoxy)benzene;
2-amino-1-(3-methoxycarbonyl-2-thioureido)-5-(3-fluorophenoxy)benzene;
2-amino-1-(3-methoxycarbonyl-2-thioureido)-4-(4-acetylphenoxy)benzene;
2-amino-1-(3-methoxycarbonyl-2-thioureido)-5-(4-acetylphenoxy)benzene;
2-amino-1-(3-methoxycarbonyl-2-thioureido)-4-(4-methylsulfinylphenoxy)benzene;
2-amino-1-(3-methoxycarbonyl-2-thioureido)-5-(4-methylsulfinylphenoxy)benzene;
2-amino-1-(3-methoxycarbonyl-2-thioureido)-4-(2-phenoxyethoxy)benzene;
2-amino-1-(3-methoxycarbonyl-2-thioureido)-5-(2-phenoxyethoxy)benzene;
2-amino-1-(3-methoxycarbonyl-2-thioureido)-4-methoxymethoxybenzene;
2-amino-1-(3-methoxycarbonyl-2-thioureido)-5-methoxymethoxybenzene;
2-amino-1-(3-methoxycarbonyl-2-thioureido)-4-ethoxymethoxybenzene;
2-amino-1-(3-methoxycarbonyl-2-thioureido)-5-ethoxymethoxybenzene;
2-amino-1-(3-methoxycarbonyl-2-thioureido)-4-methylthiomethoxybenzene;
2-amino-1-(3-methoxycarbonyl-2-thioureido)-5-methylthiomethoxybenzene;
2-amino-1-(3-methoxycarbonyl-2-thioureido)-4-methylsulfinylmethoxybenzene;
2-amino-1-(3-methoxycarbonyl-2-thioureido)-5-methylsulfinymethoxybenzene;
2-amino-1-(3-methoxycarbonyl-2-thioureido)-4-phenylthiobenzene;
2-amino-1-(3-methoxycarbonyl-2-thioureido)-4-(4-fluorophenylthio)benzene;
2-amino-1-(3-methoxycarbonyl-2-thioureido)-5-(4-fluorophenylthio)benzene;
2-amino-1-(3-methoxycarbonyl-2-thioureido)-4-methoxymethylthiobenzene;
2-amino-1-(3-methoxycarbonyl-2-thioureido)-5-methoxymethylthiobenzene;
2-amino-1-(3-methoxycarbonyl-2-thioureido)-4-ethoxymethylthiobenzene;
2-amino-1-(3-methoxycarbonyl-2-thioureido)-5-ethoxymethylthiobenzene;
2-amino-1-(3-methoxycarbonyl-2-thioureido)-4-methoxyethylthiobenzene;
2-amino-1-(3-methoxycarbonyl-2-thioureido)-5-methoxyethylthiobenzene;
2-amino-1-(3-methoxycarbonyl-2-thioureido)-4-ethoxyethylthiobenzene;
2-amino-1-(3-methoxycarbonyl-2-thioureido)-5-ethoxyethylthiobenzene;
2-amino-1-(3-methoxycarbonyl-2-thioureido)-4-phenoxyethylthiobenzene;
2-amino-1-(3-methoxycarbonyl-2-thioureido)-5-phenoxyethylthiobenzene;
2-amino-1-(3-methoxycarbonyl-2-thioureido)-4-methoxymethylsulfinylbenzene;
2-amino-1-(3-methoxycarbonyl-2-thioureido)-5-methoxymethylsulfinylbenzene;
2-amino-1-(3-methoxycarbonyl-2-thioureido)-4-methoxyethylsulfinylbenzene;
2-amino-1-(3-methoxycarbonyl-2-thioureido)-5-methoxyethylsulfinylbenzene;
2-amino-1-(3-methoxycarbonyl-2-thioureido)-4-ethoxymethylsulfinylbenzene;
2-amino-1-(3-methoxycarbonyl-2-thioureido)-5-ethoxymethylsulfinylbenzene;
2-amino-1-(3-methoxycarbonyl-2-thioureido)-4-ethoxyethylsulfinylbenzene;
2-amino-1-(3-methoxycarbonyl-2-thioureido)-5-ethoxyethylsulfinylbenzene;
2-amino-1-(3-methoxycarbonyl-2-thioureido)-4-phenoxyethylsulfinylbenzene;
2-amino-1-(3-methoxycarbonyl-2-thioureido)-5-phenoxyethylsulfinylbenzene;
2-amino-1-(3-methoxycarbonyl-2-thioureido)-4-phenylsulfinylbenzene;
2-amino-1-(3-methoxycarbonyl-2-thioureido)-5-phenylsulfinylbenzene;
2-amino-1-(3-methoxycarbonyl-2-thiouredio)-4-(4-fluorophenylsulfinyl)benzene;
2-amino-1-(3-methoxycarbonyl-2-thioureido)-5-(4-fluorophenylsulfinyl)benzene;
2-amino-1-(3-methoxycarbonyl-2-thioureido)-4-(naphth-2-ylsulfinyl)benzene;
2-amino-1-(3-methoxycarbonyl-2-thioureido)-5-(naphth-2-ylsulfinyl)benzene;
2-amino-1-(3-methoxycarbonyl-2-thioureido)-4-(2,2,2-trifluoroethylthio)benzene;
2-amino-1-(3-methoxycarbonyl-2-thioureido)-5-(2,2,2-trifluoroethylthio)benzene;

2-amino-1-(3-methoxycarbonyl-2-thioureido)-4-(2,2,3,3-tetrafluoropropylthio)benzene;

2-amino-1-(3-methoxycarbonyl-2-thioureido)-5-(2,2,3,3-tetrafluoropropylthio)benzene;

2-amino-1-(3-methoxycarbonyl-2-thioureido)-4-(2,2,2-trifluoroethylsulfinyl)benzene;

2-amino-1-(3-methoxycarbonyl-2-thioureido)-5-(2,2,2-trifluoroethylsulfinyl)benzene;

2-amino-1-(3-methoxycarbonyl-2-thioureido)-4-(2,2,3,3-tetrafluoropropylsulfinyl)benzene;

2-amino-1-(3-methoxycarbonyl-2-thioureido)-5-(2,2,3,3-tetrafluoropropylsulfinyl)benzene;

1-(3-carbomethoxy-2-thioureido)-2-(5-carboxyvaler-1-ylamido)-4-n-propylsulfinylbenzene.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE I 2.37 G. of 1-acetamido-2-nitro-4-thiocyanatobenzene is dissolved in 10 ml. of dimethylformamide under nitrogen and 0.38 g. of sodium borohydride added at 20°-30° C. The mixture is stirred for one hour and then 2.4 ml. of benzylbromide is added. After a further 2 hours the mixture is diluted with water and the product filtered off and washed with water and hexane. Recrystallation from methanol gives pure 1-acetamido-2-nitro-4-benzylthiobenzene.

2.4 G. of 1-acetamido-2-nitro-4-benzylthiobenzene is treated with 2.4 g. iron powder and 1.2 g. ferrous sulfate in a mixture of 60 ml. water and 240 ml. methanol, at reflux for 4 hours. The mixture is then filtered, the filtrate concentrated and the residue recrystallized from benzene. Pure 1-acetamido-2-amino-4-benzylthiobenzene is obtained.

1.6 G. of 1-acetamido-2-amino-4-benzylthiobenzene is dissolved in 32 ml. acetone and treated with 2.4 g. methoxycarbonylisothiocyanate. The mixture is left overnight at room temperature, then concentrated and the residue triturated with ether. Pure 1-(3-methoxycarbonyl-2-thioureido)-2-acetamido-5-benzylthiobenzene is obtained by recrystallization from methanol.

In a similar manner, using methyl iodide, ethyl iodide, propyl bromide, butyl bromide, pentyl bromide, hexyl bromide, cyclopentyl bromide, cyclohexyl bromide, 2-propenyl bromide, 2-butenyl bromide, 3-butenyl bromide, 2-pentenyl bromide, 2-hexenyl bromide, 2-propynyl bromide, 2-butynyl bromide, 3-butynyl bromide, 2-pentynyl bromide, or 2-hexynyl bromide in place of the benzyl bromide, the corresponding alkylthio, cycloalkylthio, alkenylthio, or alkynylthio compounds, including 2-acetamido-1-(3-methoxycarbonyl-2-thioureido)-5-methylthiobenzene, 2-acetamido-1-(3-methoxycarbonyl-2-thioureido)-5-ethylthiobenzene, 2-acetamido-1-(3-methoxycarbonyl-2-thioureido)-5-n-propylthiobenzene, and 2-acetamido-1-(3-methoxycarbonyl-2-thioureido)-5-n-butylthiobenzene, are prepared.

In a similar manner using any of the compounds prepared above, and substituting ethoxy carbonyl isothiocyanate, propoxy carbonyl isothiocyanate, or butoxy carbonyl isothiocyanate for the methoxy carbonyl isothiocyanate, the corresponding alkylthio, cycloalkylthio, alkenylthio, or alkynylthio compounds are prepared where R is either ethyl, propyl or butyl.

EXAMPLE II

5 G. of 1-acetamido-2-nitro-4-thiocyanatobenzene and 1.7 ml. of n-propyl bromide are added to a solution of 4.8 g. of potassium hydroxide in 70 ml. of ethanol. The mixture is left overnight at room temperature, then diluted with water. Pure 1-amino-2-nitro-4-n-propylthiobenzene is collected by filtration.

A few drops of concentrated sulfuric acid are added to a solution of 3.7 g. of 1-amino-2-nitro-4-n-propylthiobenzene in 37 ml. of acetic anhydride. The mixture is left at room temperature for 1-2 hours, then treated with a slight excess of sodium acetate and evaporated. Water is added and 1-acetamido-2-nitro-4-n-propylthiobenzene is collected by filtration.

A solution of 3.0 g. of 1-acetamido-2-nitro-4-n-propylthiobenzene in 30 ml. chloroform is cooled to −15° C. and treated with a solution of 2.5 g. of 40% peracetic acid in 4 ml. methanol. After the addition the temperature is allowed to rise slowly to 20° C whereupon the solution is washed with sodium bisulfite solution and then with sodium bicarbonate solution. The product is isolated by evaporation of the solvent and purified by treatment with ether to afford 1-acetamido2-nitro-4-n-propylsulfinylbenzene.

1.5 G. of 1-acetamido-2-nitro-4-n-propylsulfinylbenzene is treated with 3 ml. of 5N sodium hydroxide solution and sufficient methanol to effect solution. After heating on a steam bath for 15 minutes, the mixture is diluted with water, cooled and filtered, yielding 1-amino-2-nitro-4-n-propylsulfinylbenzene.

1.07 G. of 1-amino-2-nitro-4-n-propylsulfinylbenzene and 1 g. of 5% palladized charcoal in 100 ml. methanol are treated with hydrogen at atmospheric pressure until the theoretical uptake of hydrogen has occured (about 1 hour). The mixture is filtered and the filtrate evaporated to give 1,2-diamino-4-n-propylsulfinylbenzene. This is treated, in 20 ml. acetone, with 2.5 g. methoxy carbonyl isothiocyanate. The mixture is kept at room temperature overnight and then concentrated under vacuum. The residue is triturated with ether and recrystallized from acetone, yielding 1,2-bis-(3-carbomethoxy-2-thioureido)-4-n-propylsulfinylbenzene.

In a similar manner, using the alkyl halides or cycloalkyl halides referred to in Example I above in place of n-propyl bromide, the corresponding alkylsulfinyl- and cycloalkylsulfinyl- 1,2-bis-(3-carbomethoxy-2-thioureido) compounds including 1,2-bis-(3-methoxycarbonyl-2-thioureido)-4-methylsulfinylbenzene, 1,2-bis-(3-methoxycarbonyl-2-thioureido)-4-ethylsulfinylbenzene, 1,2-bis-(3-methoxycarbonyl-2-thioureido)-4-isopropylsulfinylbenzene, and 1,2-bis-(3-methoxycarbonyl-2-thioureido)-4-n butylsulfinylbenzene, are prepared. By substituting ethoxy-, propoxy- or butoxy-carbonyl isothiocyanate for the methoxy carbonyl isothiocyanate, the corresponding 4(5)-sulfinyl-1,2-bis-(carbalkoxythioureido) compounds are prepared where R is either ethyl, propyl or butyl.

EXAMPLE III

3 G. of 1-amino-4-methylthio-2-nitrobenzene as prepared, for example, in the first step of Example II is dissolved in 20 ml. acetic anhydride, 2 drops of concentrated sulfuric acid is added and the mixture left at room temperature for 1 hour. Sodium acetate is added and the mixture stripped under vacuum. The residue is treated with water and 1-acetamido-4-methylthio-2-nitrobenzene collected by filtration. It may be recrystallized from methanol or used directly in the next step. 2.26 G. of 1-acetamido-4-methylthio-2-nitrobenzene is dissolved in 20 ml. chloroform and treated at about −15°C to −10° C with 2 g. of 40% peracetic acid in 2 ml. methanol. The mixture is allowed to warm slowly to room temperature and is stirred for 4 hours, after which time it is washed with potassium bicarbonate solution and sodium bisulfite solution, dried over magnesium sulfate and stripped under vacuum. The residue is recrystallized from benzene yielding pure 1-acetamido-4-methylsulfinyl-2-nitrobenzene.

1.5 G. of 1-acetamido-4-methylsulfinyl-2-nitrobenzene is hydrogenated at one atmosphere pressure in 150 ml. methanol in the presence of 1.5 g. 5% palladized charcoal, until the theoretical uptake of hydrogen has occurred (about 30 minutes). The catalyst is filtered off and the solution stripped under vacuum. The residual 1-acetamido-2-amino-4-methylsulfinylbenzene is dissolved in 20 ml. of acetone and treated with 1.5 g. of methoxy carbonyl isothiocyanate. The mixture is left overnight and the solid product filtered off. Recrystallization from methanolchloroform yields pure 2-acetamido-1-(3-methoxycarbonyl-2-thioureido)-5-methylsulfinylbenzene.

In a similar manner using the alkylthio-, or cycloalkylthio- compounds as prepared in the first step of Example II in place of the methylthio starting compound of this Example, the corresponding alkylsulfinyl- and cycloalkylsulfinyl- compounds are prepared.

In a similar manner using propionic anhydride, butyric anhydride, valeric anhydride, or caproic anhydride in place of acetic anhydride the corresponding 1-(3-alkoxycarbonyl-2-thioureido) -2-acylamino-5-alkylsulfinyl (or 5-cycloalkylsulfinyl) benzene compounds are prepared.

EXAMPLE IV 4.0 G. of 1-acetamido-4-methylthio-2-nitrobenzene (as prepared for example in Example II) is treated in 40 ml. chloroform with 12 ml. 40% peracetic acid at room temperature. The mixture is left for 1 ½ hours, then the product is filtered off and washed with methanol, yielding pure 1-acetamido -4-methylsulfonyl-2-nitrobenzene.

4 G. of 1-acetamido-4-methylsulfonyl-2-nitrobenzene is treated with 40 ml. concentrated hydrochloric acid on the steam bath for 1 hour. The mixture is cooled and diluted with water. Pure 1-amino-4-methylsulfonyl-2-nitrobenzene is collected by filtration.

2 G. of 1-amino-4-methylsulfonyl-2-nitrobenzene is treated in 200 ml. methanol with hydrogen at 4 atmospheres pressure in the presence of Raney nickel catalyst. The catalyst is removed by filtration and the filtrate concentrated to yield pure 1,2-diamino-4-methylsulfonylbenzene.

1 G. of 1,2-diamino-4-methylsulfonylbenzene is dissolved in 100 ml. of tetrahydrofuran and treated with 3 g. of 3-methoxy carbonyl isothiocyanate. The mixture is left overnight at room temperature and then concentrated under vacuum. The residue is triturated with methanol and recrystallized from methanolchloroform,, yielding pure 1,2-bis-(3-methoxycarbonyl-2-thioureido)-4-methylsulfonylbenzene.

In a similar manner using the alkylthio-, or cycloalkylthio- compounds as prepared in the first step of Example II in place of the methylthio starting compound of this Example the corresponding alkylsulfonyl- and cycloalkylsulfonyl- compounds are prepared.

EXAMPLE V

6 G. of 1-acetamido-2-nitro-4-thiocyanatobenzene is suspended in a mixture of 30 ml. concentrated hydrochloric acid and 30 ml. methanol, and the mixture stirred at room temperature for 24 hours. The water is added and the product isolated by filtration, yielding 1-amino-2-nitro-4-thiocyanatobenzene.

4 G. of 1-amino-2-nitro-4-thiocyanatobenzene is suspended in 12 ml. concentrated hydrochloric acid and cooled to about −40° C. A solution of 24 g. stannous chloride in 12 ml. concentrated hydrochloric acid is added. The mixture is allowed to warm slowly to room temperature and after 20 minutes the product is filtered off and washed with 24 ml. 6N hydrochloric acid. The salt is dissolved in water, treated with potassium bicarbonte, and the mixture extracted with chloroform. Evaporation of the chloroform extracts followed by crystallization of the crude product from benzene yields pure 1,2-diamino-4-thiocyanatobenzene.

2.6 G. 1,2-diamino-4-thiocyanatobenzene in 48 ml. acetone is treated overnight with 8 g. methoxy carbonyl isothiocyanate at room temperature. The solution is concentrated and the residue triturated with methanol and recrystallized from methanol-chloroform, yielding pure 1,2-bis-(3-methoxycarbonyl-2-thioureido)-4-thiocyanatobenzene.

In a similar manner using ethoxy carbonyl isothiocyanate, propoxy carbonyl isothiocyanate and butoxy carbonyl isothiocyanate in place of the methoxy carbonyl isothiocyanate, 1,2-bis-(3-ethoxycarbonyl-2-thioureido)-4-thiocyanatobenzene, 1,2-bis-(3-propoxycarbonyl-2-thioureido)-4-thiocyanatobenzene, and 1,2-bis-(3-butoxycarbonyl-2-thioureido)-4-thiocyanatobenzene are respectively prepared.

EXAMPLE VI 2.0 G. of 1-amino-2-nitro-4-thiocyanatobenzene in 20 ml. acetone is treated with 3.0 g. methoxycarbonyl isothiocyanate at room temperature for 9 days. The solution is concentrated and the residue triturated with methanol and recrystallized from acetone, yielding 1-(3-methoxycarbonyl-2-thioureido)-2-nitro-4-thiocyanatobenzene.

In a similar manner using ethoxycarbonyl isothiocyanate, propoxycarbonyl isothiocyanate and butoxycarbonyl isothiocyanate in place of the methoxycarbonyl isothiocyanate, 1-(3-ethoxycarbonyl-2-thioureido)-2-nitro-4-thiocyanatobenzene, 1-(3-propoxycarbonyl-2-thioureido)-2-nitro-4-thiocyanatobenzene, and 1-(3-butoxycarbonyl-2-thioureido)-2-nitro-4-thiocyanatobenzene are respectively prepared.

1 G. of the methoxycarbonyl-, ethoxycarbonyl-, propoxycarbonyl- and butoxycarbonyl- compounds prepared above in this Example are respectively treated with 2.4 g. iron powder and 1.2 g. ferrous sulfate in a mixture of 60 ml. water and 240 ml. methanol at reflux for 4 hours. The mixture is filtered, the filtrate concentrated and the residue recrystallized to afford the corresponding 1-(3-alkoxycarbonyl-2-thioureido)-2-amino-4-thiocyanatobenzene derivatives. A few drops of concentrated sulfuric acid are added to a solution of 1 g. of each of such 1-(3-alkoxycarbonyl- 2-thioureido)-2-amino-4-thiocyanatobenzene derivatives in 5 ml. of acetic anhydride. The mixture is left at room temperature for 1-2 hours, then treated with a slight excess of sodium acetate and evaporated. The residue is treated with water and the corresponding 1-(3-alkoxycarbonyl-2-thioureido)-2-acetamido-4-thiocyanatobenzene derivatives collected by filtration.

In a similar mannner using propionic anhydride, butyric anhydride, valeric anhydride, or caproic anhydride in place of acetic anhydride, the corresponding 1-(2-alkoxycarbonyl-2-thioureido)-2-acylamino-4-thiocyanatobenzene compounds are prepared.

0.5 G. of each 1-(3-alkoxycarbonyl-2-thioureido)-2-amino-4-thiocyanatobenzene compound prepared above is treated with 1 g. succinnic anhydride in 30 ml. tetrahydrofuran at reflux for six hours. The product is filtered off from the concentrated mixture. Recrystallization yields the corresponding 1-(3-alkoxycarbonyl-2-thioureido)-2-succinamido-4-thiocyanatobenzene derivatives.

EXAMPLE VII

4 G. of 1-acetamido-4-methylsulfinyl-2-nitrobenzene prepared according to Example II is treated with 8 ml. 5N NaOH on a steam bath for 30 minutes. The reaction mixture is diluted with water, cooled and the product filtered off. The 1-amino-4-methylsulfinyl-2-nitrobenzene is pure enough for the next step but may be recrystallized from benzene if desired. The 1-amino-4methylsulfinyl-2-nitro-benzene in 200 ml. acetone is treated with 4 g. methoxy carbonyl isothiocyanate at room temperature for several days (i.e., until no starting material is present). The mixture is concentrated and the residue triturated with methanol to yield pure 1-(3-methoxycarbonyl-2-thioureido)-4-methylsulfinyl-2-nitrobenzene.

1.5 G. of 1-(3-methoxycarbonyl-2-thioureido)-4-methylsulfinyl-2-nitrobenzene is treated in a boiling mixture of 240 ml. methanol and 60 ml. water with 1.5 g. iron powder and 0.75 g. ferrous sulfate for 3 hours. The mixture is filtered and the filtrate concentrated to a small volume, and diluted with water. The white solid is collected and recrystallized from ethanol, yielding pure 2-amino-4-methylsulfinyl-1-(3-methoxycarbonyl-2-thioureido)-benzene.

In a similar manner using the 1-acetamido-2-nitro-4-alkylsulfinyl- or 4-cycloalkylsulfinyl- compounds of Example II in place of other methylsulfinyl starting material of this Example, the corresponding 1-(methoxycarbonyl-2-thioureido)-2-nitro-4-alkylsulfinylbenzene, 1-(methoxycarbonyl-2-thioureido)-2-nitro-4-cycloalkylsulfinylbenzene, 1-(methoxycarbonyl-2-thioureido)-2-amino-4-alkylsulfinylbenzene, and 1-(methoxycarbonyl-2-thioureido)-2-amino-4-cycloalkylsulfinylbenzene compounds are prepared.

Also in a similar manner, substituting ethoxy-, propoxy- or butoxy- carbonyl isothiocyanate for the methoxy carbonyl isothiocyanate of this Example, the corresponding 4-alkylsulfinyl- or 4-cycloalkylsulfinyl-1-(3-alkoxycarbonyl-2-thioureido) compounds are prepared where R is either ethyl, propyl or butyl.

EXAMPLE VIII 2.37 G. of 1-acetamido-2-nitro-4-thiocyanatobenzene in 10 ml. dimethylformamide is treated, under nitrogen, with 0.38 g. sodium borohydride at 20°-30° C. After one hour at 20°-30° C., 1.6 ml. of chloromethyl methyl ether is added. The mixture is stirred for a further 3 hour period, then diluted with water. The crude product is filtered off and recrystallized from cyclohexane, yielding 1-acetamido-2-nitro-4-methoxymethylthiobenzene.

1.4 G. of 1-acetamido-2-nitro-4-methoxymethylthiobenzene is treated on a steam bath for 15 minutes with 3 ml. 5N sodium hydroxide and 6 ml. methanol. The mixture is concentrated, extracted with chloroform and the chloroform extracts dried and stripped yielding 1-amino-2-nitro-4-methoxymethylthiobenzene as a red solid.

1.2 G. 1-amino-2-nitro-4-methoxymethylthiobenzene is reduced in 80 ml. methanol and 20 ml. water at reflux with 2.4 g. iron powder and 0.6 g. ferrous sulfate. The mixture is filtered and concentrated. The residue is recrystallized from cyclohexane, yielding pure 1,2-diamino-4-methoxymethylthiobenzene.

0.6 G. 1,2-diamino-4-methoxymethylthiobenzene is dissolved in 10 ml. acetone and treated overnight with 2 g. methoxy carbonyl isothiocyanate at room temperature. The mixture is concentrated and the residue triturated with with ether and recrystallized from benzene yielding pure 1,2-bis-(3-methoxycarbonyl-2-thioureido)-4-methoxymethylthiobenzene.

In a similar manner using chloroethyl methyl ether, chloropropyl methyl ether, chlorobutyl ether, chloromethyl ethyl ether, chloromethyl propyl ether, chloromethyl butyl ether, methylthiomethyl chloride, methylthioethyl chloride, methylthiopropyl chloride, methylthiobutyl chloride, ethylthiomethyl chloride, propylthiomethyl chloride, butylthiomethyl chloride, and ethylthioethyl chloride in place of the chloromethylmethyl ether of this Example, the corresponding 1,2-diamino-4-alkoxyalkylthiobenzene, 1,2-diamino-4-alkylthioalkylthiobenzene, 1,2-bis-(3-methoxycarbonyl-2-thioureido)-4-alkoxyalkylthiobenzene, and 1,2-bis-(3-methoxycarbonyl-2-thioureido)-4-alkylthioalkylthiobenzene compounds are prepared. By reacting the 1,2-diamino-4-alkoxyalkylthiobenzene or 1,2-diamino-4-alkylthioalkylthiobenzene compounds so prepared with ethoxy carbonyl isothiocyanate, propoxy carbonyl isothiocyanate and butoxy carbonyl isothiocyanate, the corresponding 1,2-bis-(3-alkoxycarbonyl-2-thioureido)-4-alkoxyalkylthiobenzene or 1,2-bis-(3-alkoxycarbonyl-2-thioureido)-4-alkylthioalkylthiobenzene compounds are prepared, where R is ethyl, propyl or butyl.

EXAMPLE IX

3 G. of 1-acetamido-4-n-butylthio-2-nitrobenzene (prepared according to Example I) is hydrolyzed by treatment with 6 ml. 5N NaOH and 6 ml. ethanol on the steam bath for one hour. The mixture is concentrated and extracted with chloroform. Removal of the solvent leaves 1-amino-4-n-butylthio-2-nitrobenzene as a red oil.

2.5 G. of 1-amino-4-n-butylthio-2-nitrobenzene (alternatively prepared according to Example II) is dissolved in 25 ml. acetone and treated at room temperature with 3 g. methoxy carbonyl isothiocyanate. The mixture is left overnight, stripped under vacuum and the residue triturated with methanol and recrystallized from methanol to yield pure 4-n-butylthio-1-(3-methoxycarbonyl-2-thioureido)-2-nitrobenzene.

In a similar manner, using the other 1-acetamido-2-nitro-4-alkylthio or 4-cycloalkylthio benzene compounds prepared according to Example I in place of the 4-n-butylthio starting material of this Example, the corresponding 1-(3-methoxycarbonyl-2-thioureido)-2-nitro-4-alkylthio- or 4-cycloalkylthio-benzene compounds, are prepared.

Also in a similar manner reacting methoxy-, ethoxy-, propoxy- or butoxy-carbonyl isothiocyanate with any of the alkylthio or cycloalkylthio compounds prepared above in this Example the corresponding 1-(3-alkoxycarbonyl-2-thioureido)-2-nitro-4-alkylthio- or 4-cycloalkylthio-benzene compounds are prepared where R is either methyl, ethyl, propyl or butyl.

2.5 G. of 4-n-butylthio-1-(3-methoxycarbonyl-2-thioureido)-2-nitrobenzene is treated with 2.5 g. iron powder and 1.25 g. ferrous sulfate in a refluxing mixture of 200 ml. methanol and 50 ml. water. After three hours the mixture is filtered, concentrated and diluted with water. The product is filtered off and recrystallized from ethanol yielding pure 2-amino-4-n-butylthio-1-(3-methoxycarbonyl-2-thioureido)benzene.

In a similar manner using any of the 1-(3-alkoxycarbonyl-2-thioureido)-4-alkyl (or cycloalkyl thio-2-nitrobenzene compounds prepared above as the starting material, the corresponding 2-amino derivatives thereof are prepared.

0.7 G. of 2-amino-4-n-butylthio-1-(3-methoxycarbonyl-2-thioureido)benzene is dissolved in 20 ml. tetrahydrofuran and treated with 1.5 ml. of acetyl chloride. The mixture is stripped after two hours and the residue recrystallized from methanol, yielding pure 2-acetamido-4-n-butylthio-1-(3-methoxycarbonyl-2-thioureido)benzene.

In a similar manner using any of the 1-(3-alkoxycarbonyl-2-thioureido)-4-alkyl (cycloalkyl) thio-2-aminobenzene compounds prepared above as the starting material, the corresponding 1-acetamido derivatives thereof are prepared.

Also in a similar manner using propionyl chloride, butyryl chloride, valeryl chloride, or caproyl chloride in place of acetyl chloride, the corresponding acyl-amino derivatives of the particular 1-(3-alkoxycarbonyl-2-thioureido)-2-amino-4-alkyl (or cycloalkyl) thiobenzene reactants utilized are prepared.

EXAMPLE X 5.85 G. of 1-amino-2-nitro-4-thiocyanatobenzene in 20 ml. dimethylformamide is treated, under nitrogen, with 1.14 g. sodium borohydride at 20°-30° C. After 1 ½ hours 5 ml. of propargyl bromide is added. The mixture is stirred for three hours at 20°-30° C, then diluted with water. The product, a red solid, is isolated by extraction into chloroform yielding 1-amino-2-nitro-4-propargylthiobenzene.

4.8 of 1-amino-2-nitro-4-propargylthiobenzene in 1.4 ml. concentrated hydrochloric acid is treated with a solution of 24 g. stannous chloride in 14 ml. concentrated hydrochloric acid at room temperature. After 30 minutes the mixture is treated with potassium bicarbonate and chloroform. The mixture is filtered and the chloroform extract dried and evaporated. 1,2-diamino-4-propargylthiobenzene remains as a colorless oil.

4 G. of 1,2-diamino-4-propargylthiobenzene in 40 ml. aceton is treated with 10 g. of methoxy carbonyl isothiocyanate. The mixture is left overnight at room temperature, stripped under vacuum and the residue triturated with ether. Recrystallization from methanol gives pure 1,2-bis-(3-methoxycarbonyl-2-thioureido)-4-propargylthio-benzene.

In a similar manner, using 1-chloro-2-propene, 1-chloro-2-butene, 1-chloro-3-butene, 1-chloro-2-hexene, 1-chloro-2-butyne, 1-chloro-3-butyne, 1-chloro-2-hexyne in place of propargyl bromide, the corresponding 1,2-diamino-4-alkenylthiobenzene, 1,2-diamino-4-alkynylthiobenzene, 1,2-bis-(3-methoxycarbonyl-2-thioureido)-4-alkenylthiobenzene, and 1,2-bis-(3-methoxycarbonyl-2-thioureido)-4-alkynylthiobenzene compounds are prepared. By reacting the diamino compounds so prepared with ethoxy-, propoxy-, or butoxycarbonyl isothiocyanate in place of the methoxy-carbonyl isothiocyanate, the corresponding 1,2-bis-(3-alkoxycarbonyl-2-thioureido)-4-alkenylthiobenzene and 1,2-bis-(3-alkoxycarbonyl-2-thioureido)-4-alkynylthiobenzene compounds are prepared, where R is ethyl, propyl or butyl.

EXAMPLE XI

A mixture of 2 g. sodium hydroxide, 2.4 g. methylmercaptan and 20 ml. dimethylformamide is stirred at room temperature for two hours. 3.0 g. 2-amino-4-chloro-1-nitrobenzene is added and the mixture stirred for 1 ½ hours. Water is added and the crude product filtered off. Recrystallization from methanol yields pure 2-amino-4-methylthio-1-nitrobenzene.

1.5 G. 2-amino-4-methylthio-1-nitrobenzene in 30 ml. acetone is treated with 2.5 g. methoxy carbonyl isothiocyanate. After five days the mixture is stripped under vacuum and the residue triturated with methanol yielding 1-(3-methoxycarbonyl-2-thioureido)-5-methylthio-2-nitrobenzene.

1.2 G. 1-(3-methoxycarbonyl-2-thioureido)-5-methylthio-2-nitrobenzene is treated at reflux for one hour with 1.2 g. iron powder in 240 ml. methanol containing 2.4 ml. acetic acid. The mixture is cooled, concentrated and the product isolated by filtration, washed with water and recrystallized from methanol-chloroform, yielding pure 1-(3-methoxycarbonyl-2-thioureido)-5-methylthio-2-aminobenzene.

In a similar manner substituting ethylmercaptan, propylmercaptan, butylmercaptan, pentylmercaptan, hexylmercaptan, cyclopentylmercaptan, cycloheptylmercaptan, phenylmercaptan, p-chlorophenylmercaptan, and benzylmercaptan for the methylmercaptan of this Example, the corresponding 1-(3-methoxycarbonyl-2-thioureido)-2-nitro-5-alkylthio-, 5-cycloalkylthio-, 5-phenylthio-, 5-(p-chlorophenylthio)-, and 5-benzylthio-, benzene compounds, and the corresponding 1-(3-methoxycarbonyl-2-thioureido)-2-amino-5-alkylthio, 5-cycloalkylthio, 5-phenylthio-, 5-(p-chlorophenylthio)-, and 5-benzylthio benzene compounds are prepared. Also in a similar manner by substituting ethoxy-, propoxy-, or butoxy-carbonyl isothiocyanate for methoxycarbonyl isothiocyanate, the corresponding 1-(3-alkoxycarbonyl-2-thioureido)-2-nitro (or 2-amino)-5-alkylthio (or 5-cycloalkylthio or 5-arylthio or 5-benzylthio)-benzene compounds are prepared, where R is ethyl, propyl or butyl.

EXAMPLE XII 2.53 G. 57% sodium hydride in oil suspension in 20 ml. dimethylformamide is treated with 6.2 ml. thiophenol under nitrogen. 5.0 G. 2-amino-4-chloro-1-nitrobenzene is added and the mixture stirred for three hours. Water is added and the product filtered off and washed with water and hexane. Recrystallization from methanol gives pure 2-amino-4-phenylthio-1-nitrobenzene.

1.8 G. 2-amino-4-phenylthio-1-nitrobenzene is treated with 2 g. iron powder and 1 g. ferrous sulfate in a refluxing mixture of 160 ml. methanol and 40 ml. water for six hours. The mixture is filtered and concentrated. The residue is extracted with benzene and 1,2-diamino-4-phenylthiobenzene isolated as a gum.

1.6 G. 1,2-diamino-4-phenylthiobenzene is dissolved in 30 ml. acetone and treated with 4 g. methoxycarbonyl isothiocyanate at room temperature overnight. The mixture is concentrated under vacuum and the residue triturated with ether. Recrystallization from methanol-chloroform yields pure 1,2-bis-(3-methoxycarbonyl-2-thioureido)-4-phenylthiobenzene.

In a similar manner using ethoxy-, propoxy-, and butoxy-carbonyl isothiocyanate in place of methoxy carbonyl isothiocyanate, 1,2-bis-(3-ethoxycarbonyl-2-thioureido)-4-phenylthiobenzene, 1,2-bis-(3-propoxycarbonyl-2-thioureido)-4-phenylthiobenzene, and 1,2-bis-(3-butoxycarbonyl-2-thioureido)-4-phenylthiobenzene are respectively prepared.

In a similar manner using p-chlorophenylmercaptan or benzylmercaptan in place of the thiophenol, 1,2-bis-(3-methoxycarbonyl-2-thioureido)-4-(p-chlorophenylthio)benzene and 1,2-bis-(3-methoxycarbonyl-2-thioureido)-4-benzylthiobenzene are prepared.

EXAMPLE XIII 3.0 G. 2-amino-4-phenylthio-1-nitrobenzene (prepared according to Example XII) is dissolved in 40 ml. of acetic anhydride and two drops of sulfuric acid added. The mixture is left at room temperature for two hours then neutralized with a little sodium acetate and concentrated under vacuum. Water is added to the residue and the crude product filtered off. Recrystallization from methanol gives pure 2-acetamido-4-phenylthio-1-nitrobenzene.

3.5 G. of 2-acetamido-4-phenylthio-1-nitrobenzene is dissolved in 35 ml. chloroform and treated at −25° C to −20° C with 2.5 g. 40% peracetic acid in 5 ml. methanol. The reaction mixture is allowed to warm slowly to 20°–25° C where it is held for four hours, then washed with sodium bisulfate solution and then with sodium bicarbonate solution. Evaporation of the solvent leaves 2-acetamido-4-phenylsulfinyl-1-nitrobenzene as a gum. This is treated with 20 ml. methanol and 10 ml. 5N aqueous sodium hydroxide at 20°–25° C for one hour. The mixture is diluted with water and the crude product filtered off. Recrystallization from benzene yields pure 2-amino-1-nitro-4-phenylsulfinylbenzene. 2.7 G. of 2-amino-1-nitro-4-phenylsulfinylbenzene is hydrogenated in 270 ml. methanol in the presence of 2.7 g. 5% palladized charcoal at one atmosphere pressure, until the theoretical uptake of hydrogen has occurred. The catalyst is removed by filtration and the filtrate concentrated to dryness. The residue is triturated with hot benzene, affording pure 1,2-diamino-4-phenylsulfinylbenzene.

2.1 G. 1,2-diamino-4-phenylsulfinylbenzene in 150 ml. acetone is treated with 6 g. methoxy carbonyl isothiocyanate overnight at 20°–25° C. The reaction mixture is stripped and the residue triturated with ether. Recrystallization from methanol yields pure 1,2-bis-(3-methoxycarbonyl-2-thioureido)- 4-phenylsulfinylbenzene.

In a similar manner substituting ethoxy-, propoxy-, or butoxy-carbonyl isothiocyanate for the methoxy carbonyl isothiocyanate, the corresponding 1,2-bis(3-alkoxycarbonyl-2-thioureido)-4-phenylsulfinylbenzene compounds are prepared, where R is respectively ethyl, propyl or butyl.

EXAMPLE XIV 1.26 G. 57% sodium hydride in oil suspension in 20 ml. dimethylformamide is treated with 3.9 g. p-chlorophenol. When the mixture becomes homogenous, 2.5 g. 2-amino-4-chloro-1-nitrobenzene is added and the mixture heated for five hours at 130°–135° C. The crude product is obtained by diluting the reaction mixture with water and filtering and washing with water and hexane. Recrystallization from methanol gives pure 2-amino-4-(4-chlorophenoxy)-1-nitrobenzene.

1.2 G. of 2-amino-4-(4-chlorophenoxy)-1-nitrobenzene in 3ml. concentrated hydrochloric acid is treated with a solution of 6 g. stannous chloride in 3 ml. concentrated hydrochloric acid. The mixture is heated briefly (about ten minutes) on a steam bath, then cooled and treated with potassium bicarbonate and chloroform. The chloroform layer is removed from the filtered mixture, dried and evaporated. 1,2-diamino-4-(4-chlorophenoxy)benzene is isolated as a gum. 1G. of 1,2-diamino-4-(4-chlorophenoxy)benzene in 20 ml. acetone is treated overnight at room temperature with 2.5 g. methoxy carbonyl isothiocyanate. The mixture is concentrated under vacuum and the residue triturated with methanol. Recrystallization from methanol gives pure 1,2-bis-(3-methoxycarbonyl-2-thioureido)-4-(4-chlorophenoxy)benzene.

In a similar manner using p-methoxyphenol, p-fluorophenol, m-fluorophenol, p-acetylphenol, p-methylsulfinylphenol, and p-hydroxytoluene in place of p-chlorophenol, there is obtained the corresponding 1,2-bis-(3-methoxycarbonyl-2-thioureido)-4-(4- or 3-substituted-phenoxy)benzene compounds. Also in a similar manner, substituting ethoxy-, propoxy- or butoxycarbonyl isothiocyanate in place of methoxy carbonyl isothiocyanate, the corresponding 1,2-bis-(3-alkoxycarbonyl-2-thioureido)-4-(4-substituted-phenoxy)benzene compounds can be prepared, where R is ethyl, propyl or butyl.

EXAMPLE XV 3.92 G. of 1-acetamido-4-hydroxy-2-nitrobenzene, 5.8 g. of chloromethyl methyl sulfide and 8.4 g. anhydrous potassium carbonate are refluxed overnight in acetone with stirring, evaporated to dryness, and water added and the product extracted with dichloromethane to give 1-acetamido4-methylthiomethoxy-2-nitrobenzene as an orange gum.

1.8 G. of 1-acetamido-4-methylthiomethoxy-2-nitrobenzene is treated with sodium hydroxide in methanol, warmed briefly on a steam bath for about 15 minutes until the reaction is complete, diluted with water and extracted with dichloromethane to give 1-amino-4-methylthiomethoxy-2-nitrobenzene as a red oil.

1.5 G. of 1-amino-4-methylthiomethoxy-2-nitrobenzene is treated in 100 ml. methanol with 1.5 g. iron powder and 1 ml. acetic acid at reflux, followed after one hour with a further addition of 1 ml. of acetic acid and 1.0 g. of iron powder. After one hour, the mixture is evaporated to dryness, the residue extracted with dichloromethane, filtered under nitrogen, dried over magnesium sulfate and charcoal, filtered once again, and evaporated to dryness to gie 1,2-diamino-4-methylthiomethoxybenene as a dark viscous oil.

The 1,2-diamino-4-methylthiomethoxybenzene prepared above is dissolved in 60 ml. acetone and treated overnight with 6 g. methoxycarbonyl isothiocyanate at room temperature. The mixture is concentrated and the residue stirred with 500 ml. water and the brown solid filtered off. The residue is extracted with 250 ml. dichloromethane, filtered, treated with charcoal, and recrystallized from dichloromethanebenzene to afford 1,2-bis(3-methoxycarbonyl-2-thioureido)-4-methylthiomethoxybenzene.

In a similar manner using chloroethyl methylsulfide, chloropropyl methylsulfide, chlorobutyl methylsulfide, chloromethyl ethylsulfide, chloromethyl propylsulfide, chloromethyl butylsulfide, methylthiomethyl chloride, methylthioethyl chloride, methylthiopropyl chloride, methylthiobutyl chloride, ethylthiomethyl chloride, propylthiomethyl chloride, butylthiomethyl chloride, and ethylthioethyl chloride in place of the chloromethyl methyl sulfide of this Example, the corresponding 1,2-diamino-4-alkylthioalkoxybenzene and 1,2-bis(3-methoxycarbonyl-2-thioureido)-4-alkylthioalkoxybenzene compounds are prepared. By reacting the 1,2-diamino-4-alkylthioalkoxybenzene compounds so prepared with ethoxycarbonyl isothiocyanate, propoxycarbonyl isothiocyanate, and butoxycarbonyl isothiocyanate in place of the methoxycarbonyl isothiocyanate, the corresponding 1,2-bis(alkoxycarbonyl-2-thioureido)-4-alkylthioalkoxybenzene compounds are prepared, where R is ethyl, propyl or butyl.

EXAMPLE XVI 0.7 G. of 2-amino-1-(3-methoxycarbonyl-2-thioureido)-5- phenylthiobenzene, as prepared according to Example XI, is dissolved in 20 ml. tetrahydrofuran and treated with 1.5 ml. of acetyl chloride. The mixture is stripped after two hours and the residue recrystallized from methanol, yielding 2-acetamido-1-(3-methoxycarbonyl-2-thioureido)-5-phenylthiobenzene.

In a similar manner using propionyl chloride, butyryl chlorie, valeryl chloride or caproyl chloride in place of the acetyl chloride, the corresponding 2-acylamino derivatives of 1-(3-methoxycarbonyl-2-thioureido)-5-phenylthiobenzene are prepared.

Also in a similar manner, utilizing 2-amino-1-(3-methoxycarbonyl-2-thioureido-5-(p-chlorophenylthio)-benzene (prepared in a manner similar to that described in Example XI) and acetyl chloride, there is prepared 2-acetamido-1-(3-methoxycarbonyl-2-thioureido)-5-(p-chlorophenylthio)benzene.

EXAMPLE XVII 1.0 G. of 2-amino-4-methylthio-1-(3-methoxycarbonyl-2-thioureido)benzene, as prepared according to Example IX, in 30 ml. tetrahydrofuran is treated with 1 g. succinic anhydride at reflux for six hours. The product is filtered off from the concentrated mixture. Recrystalization from methylene chloride-acetone yields 2-succinamido-4-methylthio-1-(3-methoxycarbonyl-2-thioureido)benzene.

In a similar manner utilizing 2-amino-1-(3-methoxycarbonyl-2-thioureido)-5-(p-chlorophenylthio)benzene, as prepared in a manner similar to that described in Example XI, the 2-amino-4-alkylthio (or 4-cycloalkylthio) compounds prepared according to Example IX, the 2-amino-4-alkenylthio (or 4-alkynylthio)compounds prepared according to Example XXV, the 2-amino-5-phenylthio compound prepared according to Example XI, or the 2-amino-4-benzylthio compound as prepared according to Example I in place of the 4-methylthio reactant of this Example, the corresponding 2-succinamido-1-(3-methoycarbonyl-2-thioureido)-4(5)-substituted thio compounds are prepared.

EXAMPLE XVIII

5 G. of 1-acetamido-2-nitro-4-thiocyanatobenzene and 2.8 ml. of n-butyl bromide are added to a solution of 4.8 g. of potassium hydroxide in 70 ml. of n-butanol. The mixture is left overnight at room temperature, then diluted with water. 1-Amino-2-nitro-4-n-butylthiobenzene is isolated by extraction with chloroform.

4 G. of 1-amino-2-nitro-4-n-butylthiobenzene is treated in 12 ml. concentrated hydrochloric acid with a solution of 24 g. stannous chloride in 12 ml. concentrated hydrochloric acid. The mixture is kept on the steam bath for 10 minutes, then cooled and the gummy product is washed with 12 ml. 6N hydrochloric acid. The salt is dissolved in water, treated with sodium hydroxide, and the mixture extracted with chloroform. Evaporation of the extracts followed by crystallation of the crude product from benzene yields 1,2-diamino-4-n-butylthiobenzene.

1.5 G. of 1,2-diamino-4-n-butylthiobenzene in 30 ml. acetone is treated overnight with 4.5 g. methoxy carbonyl isothiocyanate at room temperature. The solution is concentrated, and the residue triturated with methanol and recrystallized from methanol, yielding 1,2-bis-(3-methoxycarbonyl-2-thioureido)-4-n-butylthiobenzene.

In a similar manner using ethoxy carbonyl isothiocyanate, propoxy carbonyl isothiocyanate, and butoxy carbonyl isothiocyanate in place of the methoy carbonyl isothiocyanate, the corresponding 1,2-bis-(3-alkoxycarbonyl-2-thioureido)-4-n-butylthiobenzene derivatives are prepared where R is either ethyl, propyl or butyl.

In a similar manner, or as set forth in Example X, using methyl iodide, ethyl iodide, n-propyl bromide, i-propyl bromide, pentyl bromide, hexyl bromide, cyclopentyl bromide, or cyclohexyl bromide in place of the n-butyl bromide, the corresponding 4-alkylthio or 4-cycloalkylthio, compounds are prepared where R is methyl.

In a similar manner, using the 1,2-diamino compounds prepred above, and substituting ethoxy carbonyl isothiocyanate, propoxy carbonyl isothiocyanate, or butoy carbonyl isothiocyanate for the methoxy carbonyl isothiocyanate, the corresponding 4-alkylthio or 4-cycloalkylthio, compounds are prepared where R is either ethyl, propyl or butyl.

EXAMPLE XIX

2 G. of 2-acetamideo-1-nitro-4-phenylsulfinylbenzene, as prepared according to Example XIII, is treated for four hours in a refluxing mixture of 160 ml. methanol and 40 ml. water with 4 g. iron powder (added in two portions) and 1g. ferrous sulfate. The mixture is filtered, and the filtrate concentrated. The residue is dissolved in chloroform and washed with water, then the solvent is evaporated affording 2-acetamido-1-amino-4-phenylsulfinylbenzene.

1 G. of 2-acetamido-1-amino4-phenylsulfinylbenzene in 30 ml. acetone is treated overnight with 2 g. methoxycarbonyl isothiocyanate. The solution is concentrated and the residue triturated with ether. Recrystallization yields 2-acetamido-1-(3-methoxycarbonyl-2-thioureido)-4-phenylsulfinylbenzene.

In a similar manner using propionic anhydride, butyric anhydride, valeric anhydride or caproic anhydride in place of the acetic anhydride utilized in the first step of Example XIII, the corresponding 2-acylamino derivatives of 1-(3-methoxycarbonyl-2-thioureido)-4-phenyl-sulfinylbenzene are prepared.

By substituting the 1-acetamido-2-nitro-4-benzylthiobenzene as prepared in Example I for the 2-acetamido-1-nitro-4-phenylthiobenzene as used above in this Example, there is prepared 1-(3-methoxycarbonyl-2-thioureido)-2-acetamido-5-benzylsulfinylbenzene.

In a similar manner, substituting 2-amino-1-nitro-4-(p-chlorophenylthio)benzene prepared according to Example XII for the 2-amino-1-nitro-4-phenylthiobenzene of this Example, 1-(3-methoxycarbonyl-2-thioureido)-2-acetamido-5-(p-chlorophenylsulfinyl)benzene is prepared.

EXAMPLE XX

2 G. of 1-acetamido-2-nitro-4-propargylthiobenzene, prepared according to Example I, is treated in accordance with the third paragraph of Example II to afford 1-acetamido-2-nitro-4-propargylsulfinylbenzene.

2 G. of 1-acetamido-2-nitro-4-propargylsulfinylbenzene is treated in a refluxing mixture of 160 ml. methanol and 40 ml. water with 4 g. iron powder (added in two portions) and 1 g. ferrous sulfate for four hours. The mixture is filtered, and the filtrated concentrated. The residue is dissolved in chloroform and washed with water, then the solvent evaporated affording 1-acetamido-2-amino-4-propargylsulfinylbenzene.

1 G. of 1-acetamido-2-amino-4-propargylsulfinylbenzene in 30 ml. acetone is treated overnight at room temperature with 2 g. methoxy carbonyl isothiocyanate. The solution is concentrated and the residue triturated with ether. Recrystallization yields 2-acetamido-1-(3-methoxycarbonyl-2-thioureido)-5-propargylsulfinyl-benzene.

In a similar manner using the 1-acetamido-2-nitro-4-alkenyl(or alkynyl)thiobenzene compounds, prepared according to Example I, in place of the 1-acetamido-2-nitro-4-propargylthiobenzene of this Example, the corresponding 2-acetamido1-(3-methoxycarbonyl-2-thioureido)-5-alkenyl(or alkynyl)-sulfinyl benzenes are prepared.

Also in a similar manner using the 1-acetamido-2-amino-4-sulfinyl compounds prepared above, and substituting ethoxy carbonyl isothiocyanate, propoxy carbonyl isothiocyanate, or butoxy carbonyl isothiocyanate for the methoxy carbonyl isothiocyanate, the corresponding 2- acetamido-1-(3-alkoxycarbonyl-2-thioureido)-5-alkenyl(or alkynyl)-sulfinyl benzenes are prepared, where R is either ethyl, propyl or butyl.

EXAMPLE XXI

10 G. of 1-amino-5-phenylthio-2-nitrobenzene in 100 ml. of acetic anhydride is treated with 0.25 ml. of concentrated sulfuric acid. The mixture is kept at 20°–25° C for 2 hours, then neutralized with sodium acetate and the solvent removed under vacuum. The residue is washed with water and methanol and dried. The resulting 1-acetamido-5-phenylthio-2-nitrobenzene is dissolved in 100 ml. of chloroform and treated at −30° C with a solution of peracetic acid (1 equivalent) in 10 ml. of methanol. The solution is warmed slowly to 20°–25° C and kept at the temperature for 12 hours, then washed successively with a solution of sodium bisulfite and a solution of sodium carbonate. Removal of the solvent leaves a gum which is treated with a mixture of 30 ml. of 5 N. sodium hydroxide and 60 ml. of methanol at 20°–25° C for 1 hour. Dilution with water followed by filtration of the product gives 1-amino-5-phenylsulfinyl-2-nitrobenzene which is purified by recrystallization from cyclohexane.

A suspension of 5.2 g. of 1-amino-5-phenylsulfinyl-2-nitrobenzene in 50 ml. of acetone is treated at 20°–25° C with a solution of 100 ml. of methoxycarbonyl isothiocyanate (made from 0.125 mol. (each) of potassium thiocyanate and methylchloroformate) in acetone. After several days, the solvent is stripped off under vacuum and the residue triturated with ether. Recrystallization of the crude product from methanol-chloroform yields 1-(3-methoxycarbonyl-2-thioureido)-5-phenylsulfinyl-2-nitrobenzene.

2.0 G. of the above nitro compound is dissolved in a warm mixture of 200 ml. of methanol and 100 ml. of water, and 10 g. of sodium hydrosulfite is added. After 10 minutes at reflux, the solution is concentrated under vacuum and extracted with chloroform. The chloroform solution is washed with water, dried and evaporated. Recrystallization of the residue from ethanol yields 1-(3-methoxycarbonyl-2-thioureido)-5-phenylsulfinyl-2-aminobenzene.

In a similar manner, using 1-amino-5-(4-chlorophenylthio)-2-nitrobenzene, 1-amino-5-benzylthio-2-nitrobenzene, 1-amino-5-(4-fluorophenylthio)-2-nitrobenzene, 1-amino-5-(naphth-2-ylthio)-2-nitrobenzene (prepared in a similar manner to the process of Example XII) in place of the 1-amino-5-phenylthio-2-nitrobenzene above, 1-(3-methoxycarbonyl-2-thioureido)-5-(4-chlorophenylsulfinyl)-2-amino (or nitro)benzene, 1-(3-methoxycarbonyl-2-thioureido)-5-benzylsulfinyl-2-amino(or nitro)benzene, 1-(3-methoxycarbonyl-2-thioureido)-5-(4-fluorophenylsulfinyl)-2-amino(or nitro)-benzene, 1-(3-methoxycarbonyl-2-thioureido)-5-(4-naphth-2-ylsulfinyl)-2-amino(or nitro)benzene, are prepared respectively.

By treating the 2-amino compounds prepared above in the manner as set forth in the fourth paragraph of Example XIII, the corresponding 1,2-bis-(3-methoxycarbonyl-2-thioureido)-4(5)-substituted-benzene compounds including 1,2- bis-(3-methoxycarbonyl-2-thioureido)-4(5)-phenylsulfinylbenzene, are prepared.

EXAMPLE XXII 3.0 G. of 1-acetamido-2-nitro-4-(prop-2-en-1-yl-thio)-benzene, prepared according to Example I, in 30 ml. chloroform is cooled to −15° C. and treated with a solution of 2.5 g. of 40% peracetic acid in 4 ml. methanol. After the addition, the temperature is allowed to rise slowly to 20° C whereupon the solution is washed with sodium bisulfite solution and then with sodium bicarbonate solution. The product is isolated by evaporation of the solvent and purified to afford 1-acetamido-2-nitro-4-(prop-2-en-1-ylsulfinyl)benzene. This is treated with 20 ml. methanol and 10 ml. 5N aqueous sodium hydroxide at 20°–25° C. for one hour. The mixture is diluted with water and the crude product filtered off. Recrystallization yields 1-amino-2-nitro-4-(prop-2-en-1-ylsulfinyl)benzene.

2 G. of 1-amino-2-nitro-4-(prop-2-en-1-ylsulfinyl)-benzene is treated for four hours in a refluxing mixture of 160 ml. methanol and 40 ml. water with 4 g. iron powder (added in two portions) and 1 g. ferrous sulfate. The mixture is filtered, and the filtrate concentrated. The residue is dissolved in chloroform and washed with water, then the solvent evaporated affording 1,2-diamino-4-(prop-2-en-1-ylsulfinyl)benzene.

0.6 G. of 1,2-diamino-4-(prop-2-en-1-ylsulfinyl)-benzene is 30 ml. acetone is treated overnight at room temperature with 2 g. methoxy carbonyl isothiocyanate. The solution is concentrated and the residue triturated with ether. Recrystallization yields 1,2-bis-(3-methoxycarbonyl-2-thioureido)-4-(prop-2-en-1-ylsulfinyl)benzene.

In a similar manner substituting 1-acetamido-2-nitro-4-(prop-2-yn-1-ylthio)benzene for the 1-acetamido-2-nitro-4-(prop-2-en-1-ylthio)benzene for this Example, there is prepared 1,2-bis-(3-methoxycarbonyl-2-thioureido)-4-(prop-2-yn-1-ylsulfinyl)benzene.

EXAMPLE XXIII 1.5 G. of 1-amino-2-nitro-4-(prop-2-en-1-ylsulfinyl)-benzene or 1-amino-2-nitro-4-(prop-2-yn-1-ylsulfinyl)-benzene, prepared according to Example XXII, in 200 ml. acetone is treated with 4 g. methoxy carbonyl isothiocyanate at room temperature for several days (i.e., until no starting material is present). The mixture is concentrated and the residue triturated with methanol to yield 1-(3-methoxycarbonyl-2-thioureido)-2-nitro-4-(prop-2-en-1-ylsulfinyl)benzene or 1-(3-methoxycarbonyl-2-thioureido)-2-nitro-4-(prop-2-yn-sulfinyl)benzene, respectively.

1.5 G. of either of the compounds prepared above in this Example are treated for four hours in a refluxing mixture of 160 ml. methanol and 40 ml. water and 4 g. iron powder (added in two portions) and 1 g. ferrous sulfate. The mixture is filtered, and the filtrate concentrated. The residue is dissolved in chloroform and washed with water, and then the solvent evaporated affording 1-(3-methoxycarbonyl-2-thioureido)-2-amino-4-(prop-2-en-1-ylsulfinyl)-benzene or 1-(3-methoxycarbonyl-2-thioureido)-2-amino-4-(prop-2-yn-1-ylsulfinyl)-benzene, respectively.

EXAMPLE XXIV

The alkylthio compounds prepared in Examples IX--XI, XVI-XVIII above or Example XXV below are treated with two (or more) moles of peracetic acid at room temperature for two hours to afford the corresponding sulfonyl derivatives. Optionally, the alkylsulfinyl compounds prepared in Examples II, III, VII, and XX, XXII and XXIII can be treated in a similar manner to afford the corresponding alkylsulfonyl derivatives.

EXAMPLE XXV

2 G. of 1-acetamido-2-nitro-4-(prop-2-en-1-ylthio)-benzene is treated with 20 ml. methanol and 10 ml. 5N aqueous sodium hydroxide at 20°-25° C for one hour. The mixture is diluted with water and the crude product filtered off. Recrystallization from benzene yields 1-amino-2-nitro-4-(prop-2-en-1-ylthio)benzene. This latter compound in 200 ml. acetone is treated with 4 g. methoxy carbonyl isothiocyanate at room temperatue for several days (i.e., until no starting material is present). The mixture is concentrated and the residue triturated with methanol to yield 1-(3-methoxycarbonyl-2-thioureido)-2-nitro-4-(prop-2-en-1-ylthio)benzene.

1.5 G. of 1-(3-methoxycarbonyl-2-thioureido)-2-nitro-4-(prop-2-en-1-ylthio)benzene is treated for four hours in a refluxing mixture of 160 ml. methanol and 40 ml. water with 4 g. iron powder (added in two portions) and 1 g. ferrous sulfate. The mixture is filtered, and the filtrate concentrated. The residue is dissolved in chloroform and washed with water, and then the solvent is evaporated affording 1-(3-methoxycarbonyl-2-thioureido)-2-amino-4-(prop-2-en-1-yl-thio)benzene.

In a similar manner, substituting 1-acetamido-2-nitro-4-(prop-2-yn-1-ylthio)benzene for the 1-acetamido-2-nitro-4-(prop-2-en-1-ylthio)benzene of this Example, there is prepared 1-(3-methoxycarbonyl-2-thioureido)-2-nitro-4-(prop-2-yn-1-yl-thio)benzene and 2-amino-1-(3-methoxycarbonyl-2-thioureido)-4-(prop-2-yn-1-ylthio)benzene.

EXAMPLE XXVI

1 G. of 1-amino-2-nitro-4-methoxymethylthiobenzene, prepared according to Example VIII, in 50 ml. acetone is treated with 3 g. methoxy carbonyl isothiocyanate at room temperature for several days. The solution is concentrated and the residue triturated with methanol and recrystallized from acetone to afford 1-(3-methoxycarbonyl-2-thioureido)-2-nitro-4-methoxymethylthiobenzene. This latter compound is treated for four hours in a refluxing mixture of 160 ml. methanol and 40 ml. water with 4 g. iron powder (added in two portions) and 1 g. ferrous sulfate. The mixture is filtered, and the filtrate concentrated. The residue is dissolved in chloroform, washed with water, then the solvent is evaporated to afford 2-amino-1-(3-methoxycarbonyl-2-thioureido)-4-methoxymethylthiobenzene.

1.5 G. of 1-acetamido-2-nitro-4-methoxymethylthiobenzene, also prepared according to Example VIII, is treated for 4 hours in a refluxing mixture of 160 ml. methanol and 40 ml. water with 4 g. of iron powder (added in two portions) and 1 g. ferrous sulfate. The mixture is filtered, and the filtrate concentrated. The residue is dissolved in chloroform and washed with water, then the solvent evaporated to afford 1-acetamido-2-amino-4-methoxymethylthiobenzene.

1.0 G. of 1-acetamido-2-amino-4-methoxymethylthiobenzene in 30 ml. acetone is treated overnight with 2 g. methoxy carbonyl isothiocyanate at room temperature. The solution is concentrated and the residue triturated with ether. Recrystallization affords 2-acetamido-1-(3-methoxycarbonyl-2-thioureido)-5-methoxymethylthiobenzene.

The 2-amino-1-(3-methoxycarbonyl-2-thioureido)-4-methoxymethylthiobenzene produced above is treated in accordance with the first paragraph of Example XVII to afford 1- (3-methoxycarbonyl-2-thioureido)-4-methoxymethylthio-2-succinamido-benzene.

In a similar manner, substituting 2,2,2-trifluoro-1-iodoethane, 2,2,3,3-tetrafluoro-1-iodopropane, chloromethyl ethyl ether, or chloroethyl phenyl ether for the chloromethyl methyl ether of the first paragraph of Example VIII, and using the 1-amino(or acetamido) 2-nitro compounds prepared according to the procedure of Example VIII in the process of this Example, with optional heating during the alkylation step, the following compounds are prepared: 1-(3-methoxycarbonyl-2-thioureido)-2-amino (or acetamido or succinamido)-4-(2,2,2-trifluoroethylthio)-benzene, 1-(3-methoxycarbonyl-2-thioureido)-2-amino(or acetamido or succinamido)-4-(2,2,3,3-tetrafluoropropylthio)-benzene, 1-(3-methoxycarbonyl-2-thioureido)-2-amino(or acetamido or succinamido)-4-ethoxymethylthiobenzene, and 1-(3-methoxycarbonyl-2-thioureido)-2-amino(or acetamido or succinamido)-4-phenoxyethylthiobenzene.

EXAMPLE XXVII

2 G. of 1-acetamido (or 1-amino)-2-nitro-4-thiocyanatobenzene is treated with 10 ml. of cold concentrated sulfuric acid. The solution is held at 0°-5° C. for 24 hours then poured onto ice. The crude product is collected by filtration, and recrystallization from methanol affords 1-amino-4-carbamoylthio-2-nitrobenzene.

1 G. of 1-amino-4-carbamoylthio-2-nitrobenzene in 20 ml. acetone is treated with 3.0 g. methoxy carbonyl isothiocyanate at room temperature for several days. The solution is concentrated and the residue triturated with methanol to afford 4-carbamoylthio-1-(3-methoxycarbonyl-2-thioureido)-2-nitrobenzene.

1.5 G. of 4-carbamoylthio-1-(3-methoxycarbonyl-2-thioureido)-2-nitrobenzene is treated for four hours in a refluxing mixture of 160 ml. methanol and 40 ml. water and with 4 g. iron powder (added in two portions) and 1 g. ferrous sulfate. The mixture is filtered, and the filtrate concentrated. The residue is dissolved in chloroform and washed with water, then the solvent evaporated affording 2-amino-4-carbamoylthio-1-(3-methoxycarbonyl-2-thioureido)-benzene.

0.7 G. of 2-amino-4-carbamoylthio-1-(3-methoxycarbonyl-2-thioureido)benzene is treated with 1.5 ml. of acetyl chloride. The mixture is stripped after two hours and the residue recrystallized to afford 2-acetamido-4-carbamoylthio-1-(3-methoxycarbonyl-2-thioureido)-benzene.

0.5 G. of 2-amino-4-carbamoylthio-1-(3-methoxycarbonyl-2-thioureido)benzene is treated with 1 g. of succinic anhydride and refluxed for six hours. The product is filtered off from the concentrated mixture. Recrystallization affords 4-carbamoylthio-1-(3-methoxycarbonyl-2-thioureido)-2-succinamidobenzene.

In a similar manner, substituting 1-amino-4-carbamoylthio-2-nitrobenzene for the 4-carbamoylthio-1-(3-methoxycarbonyl-2-thioureido)-2-nitrobenzene in the iron reduction step, 1,2-diamino-4-carbamoylthiobenzene is prepared. 0.5 G. of this latter compound in 30 ml. acetone is treated overnight with 2 g. methoxy carbonyl isothiocyanate at room temperature. The solution is concentrated and the residue triturated with ether. Recrystallization yields 4-carbamoylthio-1,2-bis-(3-methoxycarbonyl-2-thioureido)-benzene.

EXAMPLE XXVIII

The 1-(3-alkoxycarbonyl-2-thioureido)-2-amino-4(5)-sulfinyl compounds prepared according to Examples VII, XXI and XXIII are treated in accordance with the first paragraph of Example XVII to afford the corresponding 1-(3-alkoxycarbonyl-2-thioureido)-2-succinamido-4(5)-sulfinylbenzene derivatives.

EXAMPLE XXIX

The 1-(3-alkoxycarbonyl-2-thioureido)-2-amino-4(5)-sulfonyl derivatives prepared according to Example XXIV are treated in accordance with the first paragraph of Example XVII to afford the corresponding 1-(3-alkoxycarbonyl-2-thioureido)-2-succinamido-4(5)-sulfonyl derivatives.

EXAMPLE XXX

1-Amino-4-methylthiomethoxy-2-nitrobenzene, prepared according to Example XV, is treated with 3.0 g. methoxy carbonyl isothiocyanate at room temperature for nine days. The solution is concentrated and the residue triturated with ether and recrystallized to afford 1-(3-methoxycarbonyl-2-thioureido)-4-methylthiomethoxy-2-nitrobenzene. This latter compound is treated in accordance with the iron reduction technique set forth in the third paragraph of Example XIX to afford 2-amino-1-(3-methoxycarbonyl-2-thioureido)-4-methylthiomethoxybenzene. This latter compound is treated in accordance with the first paragraph of Example XVI to afford 2-acetamido-1-(3-methoxycarbonyl-2-thioureido)-4-methylthiomethoxybenzene.

2-Amino-1-(3-methoxycarbonyl-2-thioureido)-4-methylthiomethoxybenzene is treated in accordance with the first paragraph of Example XVII to afford 1-(3-methoxycarbonyl-2-thioureido)-4-methylthiomethoxy-2-succinamido-benzene.

EXAMPLE XXXI 1.9 G. of 1-acetamido-4-hydroxy-2-nitrobenzene, and 10 g. anhydrous potassium carbonate were stirred at room temperature in 75 ml. acetone and treated with 5 ml. chloromethyl methyl ether over 10 minutes. After a further 10 minutes, the mixture was filtered, evaporated to dryness, and the product filtered through silica gel eluting with 1% methanol to afford 1-acetamido-4-methoxymethoxy-2-nitrobenzene.

The resulting 1-acetamido-4-methoxymethoxy-2-nitro-benzene is treated with sodium hydroxide in methanol, warmed briefly on a steam bath for about 15 minutes until the reaction is complete, diluted with water and extracted with dichloromethane to afford 1-amino-4methoxymethoxy-2-nitrobenzene. This latter compound is treated in accordance with the first paragraph of Example VI to afford 1-(3-methoxycarbonyl-2-thioureido)-4-methoxymethoxy-2-nitrobenzene. This latter compound is reduced in accordance with the iron reduction technique as set forth in the third paragraph of Example XIX to afford 2-amino-1-(3-methoxycarbonyl-2-thioureido)-4-methoxymethoxybenzene. This latter compound is treated in accordance with the first paragraph of Example XVI to afford 2-acetamido-1-(3-methoxycarbonyl-2-thioureido)-4-methoxymethoxybenzene.

2-Amino-1-(3-methoxycarbonyl-2-thioureido)-4-methoxymethoxybenzene is treated in accordance with the first paragraph of Example XVII to afford 1-(3-methoxycarbonyl-2-thioureido)-4-methoxymethoxy-2-succinamidobenzene.

1-Amino-4-methoxymethoxy-2-nitrobenzene is treated in accordance with the catalytic hydrogenation technique set forth in the third paragraph of Example III, and the fourth paragraph of Example XV to afford 1,2-bis-(3-methoxycarbonyl-2-thioureido)-4-methoxymethoxybenzene.

EXAMPLE XXXII

The 1-amino-4-methylthiomethylthio-2-nitrobenzene prepared according to Example VIII is treated with methoxy carbonyl isothiocyanate according to the first paragraph of Example VI to afford 1-(3-methoxycarbonyl-2-thioureido)-4-methylthiomethylthio-2-nitrobenzene. This latter compound is treated according to the iron reduction technique set forth in the third paragraph of Example XIX to afford 2-amino-1-(3-methoxycarbonyl-2-thioureido)-4-methylthiomethylthiobenzene. This latter compound is treated in accordance with the first paragraph of Example XVII to afford 1-(3-methoxycarbonyl-2-thioureido)-4-methylthiomethylthio-2-succinamidobenzene.

The 2-amino-1-(3-methoxycarbonyl)-2-thioureido)-4-methylthiomethylthiobenzene is treated in accordance with the first paragraph of Example XVI to afford 2-acetamido-1-(3-methoxycarbonyl-2-thioureido)-4-methylthiomethylthiobenzene.

EXAMPLE XXXIII

2-Amino-4-(4-chlorophenoxy)-1-nitrobenzene of Example XIV is treated in accordance with the first paragraph of Example VI to afford 5-(4-chlorophenoxy)-1-(3-methoxycarbonyl-2-thioureido)-2-nitrobenzene. This latter compound is treated in accordance with the iron reduction technique set forth in the third paragraph of Example XIX to afford 2-amino-5-(4-chlorophenoxy)-1-(3-methoxycarbonyl-2-thioureido)benzene. This latter compound is treated in accordance with the first paragraph of Example XVI to afford 2-acetamido-5-(4-chlorophenoxy)-1-(3-methoxycarbonyl-2-thioureido)-benzene. The 2-amino compound prepared above is treated in accordance with the first paragraph of Example XVII to afford 5-(4-chlorophenoxy)-1-(3-methoxycarbonyl-2-thioureido)-2-succinamidobenzene.

EXAMPLE XXXIV

Example XIV is repeated except phenol is substituted for the p-chlorophenol to afford 2-amino-4-phenoxy-1-nitrobenzene and 1,2-bis-(3-methoxycarbonyl-2-thioureido)-4-phenoxybenzene.

2-Amino-4-phenoxy-1-nitrobenzene is treated in accordance with the first paragraph of Example VI to afford 1-(3-methoxycarbonyl-2-thioureido)-2-nitro-5-phenoxybenzene. This latter compound is treated in accordance with the iron reduction technique set forth in the third paragraph of Example XIX to afford 2-amino-1-(3-methoxycarbonyl-2-thioureido)-5-phenoxybenzene. This latter compound is treated in accordance with the first paragraph of Example XVI to afford 2-acetamido-1-(3-methoxycarbonyl-2-thioureido)-5-phenoxybenzene.

The 2-amino compound prepared above is treated in accordance with the first paragraph of Example XVII to afford 1-(3-methoxycarbonyl-2-thioureido)-5-phenoxy-2-succinamidobenzene.

EXAMPLE XXXV 2.94 G. of 1-acetamido-4-hydroxy-2-nitrobenzene, 4.0 g. n-butyl bromide, and 4.2 g. of anhydrous potassium carbonate in 100 ml. of acetone are refluxed overnight with stirring. The mixture is evaporated, diluted with water and extracted with ether to afford 1-acetamido-4-n-butoxy-2-nitrobenzene. This latter compound is treated in accordance with the second paragraph of Example XXXI to afford 1-amino-4-n-butoxy-2-nitrobenzene. This latter compound is treated in accordance with the first paragraph of Example VI to afford 4-n-butoxy-1-(3-methoxycarbonyl-2-thioureido)-2-nitrobenzene. This latter compound is treated in accordance with the iron reduction technique set forth in the third paragraph of Example XIX to afford 2-amino-4-n-butoxy-1-(3-methoxycarbonyl-2-thioureido)benzene. This latter compound is treated in accordance with the first paragraph of Example XVII to afford 4-n-butoxy-1-(3-methoxycarbonyl-2-thioureido)-2-succinamidobenzene.

The 1-acetamido-4-n-butoxy-2-nitrobenzene prepared above is treated in accordance with the third paragraph of Example III to afford 2-acetamido-5-n-butoxy-1-(3-methoxycarbonyl-2-thioureido)benzene.

In a similar manner using ethyl iodide, propyl bromide, pentyl bromide, hexyl bromide, cyclopentyl bromide, and cyclohexyl bromide in place of the n-butyl bromide, the corresponding 4-alkoxy(or 4-cycloalkoxy)compounds are prepared.

Also in a similar manner, substituting 2-propenyl bromide or 2-propynyl bromide for the n-butyl bromide, the corresponding 4-(prop-2-en-1-yloxy) or the corresponding 4-(prop-2-yn-1-yloxy)compounds are respectively prepared.

EXAMPLE XXXVI 2.1 G. of 1-amino-4-n-butoxy-2-nitrobenzene, prepared according to Example XXXV, and 1 g. of 5% palladized charcoal in 100 ml. methanol are treated with hydrogen at atmospheric pressure until the theoretical uptake of hydrogen has occurred. The mixture is filtered and the filtrate evaporated to give 1,2-diamino-4-n-butoxybenzene. This is treated, in 60 ml. acetone, with 7.0 g. methoxycarbonyl isothiocyanate. The mixture is kept at room temperature overnight and then concentrated under vacuum. The residue is stirred with water, filtered and recrystallized from dichloromethane/benzene yielding 1,2-bis-(3-methoxycarbonyl-2-thioureido)-4-n-butoxybenzene.

In a similar manner, substituting ethyl iodide, propyl bromide, pentyl bromide, hexyl bromide, cyclopentyl bromide, and cyclohexyl bromide for the n-butyl bromide, the corresponding 4-alkoxy (or 4-cycloalkoxy) compounds are prepared.

Also in a similar manner, substituting 2-propynyl bromide or 2-propenyl bromide for the n-butyl bromide, the corresponding 4-(prop-2-en-1-yloxy) or 4-(prop-2-yn-1-yloxy) compounds are respectively prepared.

EXAMPLE XXXVII 3.0 G. 1-amino-4-hydroxy-2-nitrobenzene in 80 ml. aqueous ethanol, containing 0.80 g. sodium hydroxide, is reacted with 4.0 g. phenacyl bromide on a steam bath under nitrogen atmosphere for 2 hours, water is added and the product collected by filtration to afford 1-amino-2-nitro-4-phenacyloxybenzene. This latter compound is hydrogenated at one atmosphere pressure in 150 ml. methanol in the presence of hydrochloric acid and 2.0 g. palladized charcoal until the theoretical uptake of hydrogen has occurred. The catalyst is filtered off and the solution stripped uner vacuum to afford 1,2-diamino-4-[1-(2-hydroxy-2-phenyl)ethoxy]benzene. This latter compound is treated overnight at room temperature with 12 g. methoxy carbonyl isothiocyanate in 120 ml. acetone. The solution is evaporated and the residue triturated with water. Recrystallization from methanol yields 1,2-bis(3-methoxycarbonyl-2-thioureido)-4-[1-(2-hydroxy-2-phenyl)ethoxy]benzene.

EXAMPLE XXXVIII

1-Acetamido-2-nitro-4-phenoxybenzene is treated with 20 ml. methanol and 10 ml. 5 N aqueous sodium hydroxide at 20°-25° C for one hour. The mixture is diluted with water and the crude product filtered off. Recrystallization yields 1-amino-2-nitro-4-phenoxybenzene. This latter compound is treated in accordance with the first paragraph of Example VI to afford 1-(3-methoxycarbonyl-2-thioureido)-2-nitro-4-phenoxybenzene.

1-Acetamido-2-nitro-4-phenoxybenzene is treated in accordance with the catalytic hydrogenation technique set forth in the third paragraph of Example III to afford 1-acetamido-2-amino-4-phenoxybenzene. This latter compound is treated in accordance with the third paragraph of Example I to afford 2-acetamido-1-(3-methoxycarbonyl-2-thioureido)-4-phenoxybenzene.

1-Acetamido-2-amino-4-phenoxybenzene is treated with hydrochloric acid in aqueous methanol to afford 1,2-diamino-4-phenoxybenzene which, in turn, is reacted with methoxycarbonyl isothiocyanate in accordance with the technique set forth in the third paragraph of Example XIV to afford 1,2-bis(3-methoxycarbonyl-2-thioureido)-4-phenoxybenzene.

EXAMPLE XXXIX 2.94 G. of 1-acetamido-4-hydroxy-2-nitrobenzene, 4.2 g. anhydrous potassium carbonate and 5.13 g. benzyl bromide were refluxed overnight with stirring in 100 ml. acetone. Evaporation and extraction of the residue with dichloromethane affords 1-acetamido-4-benzyloxy-2-nitrobenzene. This latter compound is treated with sodium hydroxide in methanol, warmed briefly on a steam bath for about 15 minutes until the reaction is complete, diluted with water and extracted with dichloromethane to afford 1-amino-4-benzyloxy-2-nitrobenzene. This latter compound is treated for 4 hours in a refluxing hydrochloric acid acidified mixture of 160 ml. methanol and 40 ml. water with 4 g. iron powder (added in two portions) and 1 g. ferrous sulfate. The mixture is poured into 150 ml. concentrated ammonia, then extracted with chloroform to afford 1,2-diamino-4-benzyloxybenzene. This latter compound is treated in accordance with the fourth paragraph of Example XV to afford 4-benzyloxy-1,2-bis(3-methoxycarbonyl-2-thioureido)benzene.

1-Acetamido-4-benzyloxy-2-nitrobenzene is treated with 100 ml. methanol with 1.5 g. iron powder and 1 ml. acetic acid at reflux, followed after one hour with a further addition of 1 ml. of acetic acid and 1.0 g. of iron powder to afford 1-acetamido-2-amino-4-benzyloxybenzene. This latter compound is treated in accordance with the third paragraph of Example I to afford 2-acetamido-5-benzyloxy-1-(3-methoxycarbonyl-2-thioureido)benzene.

EXAMPLE XL 7.7 G. of acetic anhydride is added to a solution of 15.0 g. of 4-phenylthioaniline in 250ml. of chloroform and the solution is stirred for ½ hour. The solution is cooled to 0° C and 15.3 g. of 38% peracetic acid in acetic acid solution is added dropwise. The solution is stirred for 1 hour and is evaporated to dryness to yield 4-phenylsulfinylacetanilide.

A solution of 19.0g. 4-phenylsulfinylacetanilide in 12ml. of acetic acid, 15ml. of acetic anhydride and 0.5ml of concentrated sulfuric acid is treated at 0° C with a solution of 5.3 g. of 90% nitric acid in 8ml. of acetic acid. The solution is stirred for one hour and is poured onto ice. The mixture is extracted with methylene chloride and the organic layers are combined and evaporated to give 2-nitro-4-phenylsulfinylacetanilide as an oil.

A solution of 15.0 g. of 2-nitro-4-phenylsulfinylacetanilide in 250ml. of methanol is treated with 40ml. of 5 N. sodium hydroxide solution. The solution is heated for ½ hour and is then diluted with water. The mixture is extracted with methylene chloride and the organic layers are combined and evaporated to give an oil. Chromatography yields 2-nitro-4-phenylsulfinylaniline.

2.6 G. of 2-nitro-4-phenylsulfinylaniline is dissolved in 25ml. of acetone and treated at 20°-25° C with 60 ml. of a solution of methoxycarbonyl isothiocyanate (made from 0.075 mol. (each) of potassium thiocyanate and methylchloroformate in acetone). After several days, the solvent is evaporated and the residue triturated with ether. Recrystallization from methanol-chloroform yields 2-nitro-4-phenylsulfinyl-1-(3-methoxycarbonyl-2-thioureido)benzene.

1.5 G. of 2-nitro-4-phenysulfinyl-1-(3-methoxycarbonyl-2-thioureido)benzene is dissolved in a hot mixture of 450ml. of methanol and 200ml. of water. 15 G. of sodium hydrosulfite is added and, after boiling for 10 minutes, the solution is concentrated. The mixture is diluted with water, extracted thoroughly with chloroform and the product isolated by evaporation of the chloroform. Recrystallizing from methanol-chloroform yields 2-amino-1-(3-methoxycarbonyl-2-thioureido)-4-phenylsulfinylbenzene.

In a similar manner, substituting 4-(4-fluorophenylthio)aniline or 4-(naphth-2-ylthio)aniline (prepared by reduction of the corresponding nitro-compounds) for the 4-phenylthioaniline above, there is obtained 1-(3-methoxycarbonyl-2-thioureido)-2-nitro (or amino)-4-(4-fluorophenylsulfinyl)benzene and 1-(3-methoxycarbonyl-2-thioureido)-2-nitro (or amino)-4-(naphth-2-ylsulfinyl)benzene, respectively.

Reduction of the amino compounds prepared above, for example, with iron powder in acetic acid-methanol at reflux, affords the corresponding 4-substituted-thio compounds, for example, 1-(3-methoxycarbonyl-2-thioureido)-2-amino-4-phenylthiobenzene and 1-(3-methoxycarbonyl-2-thioureido)-2-amino-4-(4-fluorophenylthio)benzene.

EXAMPLE XLI

Nitration of 4-chloro-4'-acetamidodiphenyl ether with nitric acid (S.G. 1.5) in acetic acid as described by Scarborough (J. Chem. Soc. p. 2361, 1929) yields 4'-chloro-3-nitro-4-acetamidodiphenyl ether.

Hydrolysis with ethanolic hydrochloric acid, or methanolic sodium hydroxide, yields 4'-chloro-3-nitro-4-amino diphenylether. Reaction with methoxycarbonyl isothiocyanate in acetone for several days (as per Example XL) affords 4'-chloro-3-nitro-4-(3-methoxycarbonyl-2-thioureido)-diphenyl ether which is reduced with sodium hydrosulfite as per Example XL (or with iron-ferrous sulfate as per Example VII) to give 2-amino-4-(4-chloro-phenoxy)-1-(3-methoxycarbonyl-2-thioureido)benzene.

Reacting phenol or an appropriately substituted phenol, such as 4-fluorophenol, 3-fluorophenol, 4-methylsulfinylphenol, or 4-acetylphenol, with 2-amino-4-chloro-1-nitrobenzene in the presence of sodium hydride in dimethylformanide, in similar manner to the first paragraph of Example XIV, affords the corresponding 2-amino-4-phenoxy (or substituted-phenoxy)-1-nitrobenzene. Reaction with methoxycarbonyl isothiocyanate, as above, will afford the corresponding 1-(3-methoxycarbonyl-2-thioureido)-2-nitro-5-phenoxy (or substituted-phenoxy)benzenes. Reduction of the 2-nitro group affords the corresponding 1-(3-methoxycarbonyl-2-thioureido)-2-amino-5-phenoxy (or substituted-phenoxy)benzenes. The 1-nitro group of the 2-amino-4-phenoxy (or substituted-phenoxy)-1-nitrobenzenes prepared above can be reduced to afford the corresponding 1,2-diamino compounds which can be reacted with methoxycarbonyl isothiocyanate to afford the corresponding 1,2-bis-(3-methoxycarbonyl-2-thioureido)-4-phenoxy (or substituted-phenoxy)benzenes.

EXAMPLE XLII

A mixture of 2.0 g. of 4-acetamido-3-nitrophenol, 2.2 g. of β-bromophenetole, 3 g. of potassium carbonate, and 20 ml. of dimethylformanide is heated under nitrogen for 16 hours at 110° C. The mixture is cooled and poured into ice water. The precipitated solid is collected, washed with water, and dried to give 2-nitro-4-(2-phenoxyethoxy)-aniline.

A solution of 3.1 g. of 2-nitro-4-(2-phenoxyethoxy)-aniline in 20 ml. of methanol is treated with 6 ml. of 5 N. sodium hydroxide solution. The mixture is heated for ½ hour, diluted with cold water and 1-amino-2-nitro-4-(2-phenoxyethoxy)benzene isolated by filtration.

The 1-amino-2-nitro-4-(2-phenoxyethoxy)benzene so obtained is treated with methoxycarbonyl isothiocyanate (as per Example XL) to afford 1-(3-methoxycarbonyl-2-thioureido)-2-nitro-4-(2-phenoxyethoxy)benzene which is reduced with sodium hydrosulfite (as per Example XXI) or iron-ferrous sulfate (as per Example VII) to afford 1-(3-methoxycarbonyl-2-thioureido)-2-amino-4-(2-phenoxyethoxy)benzene. The latter compound is further reacted with another equivalent of methoxycarbonyl isothiocyanate to afford 1,2-bis-(3-methoxycarbonyl-2-thioureido)-4-(2-phenoxyethoxy)benzene.

In a similar manner, substituting chloromethyl methyl ether, chloromethyl ethyl ether, chloromethyl methyl sulfide, or chloromethyl methyl sulfoxide for the β-bromophenetole, 1-(3-methoxycarbonyl-2-thioureido)-2-nitro(or amino)-4-methoxymethoxybenzene, 1-(3-methoxycarbonyl-2-thioureido)-2-nitro(or amino)-4-ethoxymethoxybenzene, 1-(3-methoxycarbonyl-2-thioureido)-2-nitro(or amino)-4-methylthiomethoxybenzene, 1-(3-methoxycarbonyl-2-thioureido)-2-nitro(or amino)-4-methylsulfinylmethoxybenzene, and the 1,2-bis-(3-methoxycarbonyl-2-thioureido) counterparts thereof are respectively prepared.

EXAMPLE XLIII

5 G. of 1-amino-2-nitro-4-thiocyanatobenzene in 20 ml. of dimethylformamide is treated under nitrogen with 0.97 g. of sodium borohydride in 10 ml. of dimethylformamide at 20°–30° C. After 1 hour at 20°–25° C, 6 g. of 2,2,3,3-tetrafluoro-1-iodopropane is added and the mixture is heated at 100° C for 4 hours. The mixture is cooled, diluted with water and extracted with chloroform. Evaporation of the dried chloroform solution yields 2-nitro-4-(2,2,3,3-tetrafluoropropylthio)aniline as an oil. Acetylation of the latter compound in acetic anhydride with sulfuric acid catalysis according to the first paragraph of Example XXI yields 1-acetamido-2-nitro-4-(2,2,3,3-tetrafluoropropylthio)benzene which can be isolated by extraction into chloroform. Alternatively, this may be prepared by substituting 1-acetamido-2-nitro-4-thiocyanatobenzene in the above alkylation reaction.

In similar manner to the procedure set forth in the first three paragraphs of Example XXI, 1-(3-methoxycarbonyl-2-thioureido)-2-nitro(or amino)-4-(2,2,3,3-tetrafluoropropylsulfinyl)benzene are prepared. Substituting the appropriate starting materials prepared in Example XXI, the following compounds: 1-(3-methoxycarbonyl-2-thioureido)-2-nitro (or amino)-4-(2,2,2-trifluoroethylsulfinyl)benzene, 1-(3-methoxycarbonyl-2-thioureido)-2-nitro(or amino)-4-phenoxyethylsulfinyl-benzene, 1-(3-methoxycarbonyl-2-thioureido)-2-nitro(or amino)-4-ethoxyethylsulfinylbenzene, and 1-(3-methoxycarbonyl-2-thioureido)-2-nitro(or amino)-4-methoxymethylsulfinylbenzene are prepared, as are the 1,2-bis(3-methoxycarbonyl-2-thioureido) derivatives of the 2-amino compounds when such 2-amino compounds are reacted with another equivalent of methoxycarbonyl isothiocyanate.

Using the methoxymethylthio compounds prepared in Example VIII or the methylthiomethoxy compounds prepared in Example XV as starting materials at the appropriate point in the procedure of this Example, there are prepared, in a similar manner, 1-(3-methoxycarbonyl-2-thioureido)-2-nitro (or amino)-4-methoxymethylsulfinylbenzene and 1-(3-methoxycarbonyl-2-thioureido)-2-nitro(or amino)-4-methylsulfinylmethoxybenzene, and the 1,2-bis(3-methoxycarbonyl-2-thioureido) derivatives of the 2-amino compounds when such 2-amino compounds are reacted with another equivalent of methoxycarbonyl isothiocyanate.

EXAMPLE XLIV

In a similar manner to the procedure of Example XII substituting para-fluorothiophenol and naphth-2-ylmercaptan for the thiophenol, 1,2-bis(3-methoxycarbonyl-2-thioureido)-4-(4-fluorophenylthio)benzene and 1,2-bis(3-methoxycarbonyl-2-thioureido)-4-(naphth-2-ylthio)benzene are respectively prepared.

EXAMPLE XLV

In a similar manner to the procedure of Example XXXI substituting chloromethyl ethyl ether or chloromethyl methyl sulfide for the chloromethyl methyl ether, the corresponding 1-(3-methoxycarbonyl-2-thioureido)-2-nitro(amino, acetamido or succinamido)-4-ethoxymethoxybenzenes and 1-(3-methoxycarbonyl-2-thioureido)-2-nitro(amino, acetamido, or succinamido)-4-methylthiomethoxybenzenes are prepared, respectively. The 1,2-bis(3-methoxycarbonyl-2-thioureido) derivatives of the 2-amino compounds are prepared by reaction with a further equivalent of methoxycarbonyl isothiocyanate.

EXAMPLE XLVI

The 2-amino-1-(3-methoxycarbonyl-2-thioureido)-5-substituted phenoxybenzenes of Example XLI are treated in accordance with the first paragraph of Example XVI or the first paragraph of Example XVII to afford the corresponding 2-acetamido or 2-succinamido derivatives thereof, respectively.

EXAMPLE XLVII

2-Amino-4-phenylthio-1-nitrobenzene of Example XII is treated in accordance with the first paragraph of Example VI, the third paragraph of Example XIX, the first paragraph of Example XVI, and the first paragraph of Example XVII to afford, respectively, 1-(3-methoxycarbonyl-2-thioureido)-2-nitro-5-phenylthiobenzene, 2-amino-1-(3-methoxycarbonyl-2-thioureido)-5-phenylthiobenzene, 2-acetamido-1-(3-methoxycarbonyl-2-thioureido)-5-phenylthiobenzene, and 1-(3-methoxycarbonyl-2-thioureido)-2-succinamido-5-phenylthiobenzene.

In similar manner, substituting p-fluorophenol mercaptan for the thiophenol of Example XII, 2-amino-4-(4-fluorophenylthio)-1-nitrobenzene is prepared. Substituting this latter compound in the steps set forth above, there are prepared the corresponding 5-(4-fluorophenylthio) compounds.

The corresponding 1,2-bis(3-methoxycarbonyl-2-thioureido) compounds can be prepared by reacting the 2-amino compounds with a further equivalent of methoxycarbonyl isothiocyanate.

EXAMPLE XLVIII

A mixture of 5 g. of 2-nitro-5-chloroaniline, 7.5 g. of sodium sulfide monohydrate in 25 ml. of ethanol and 25 ml. of water is refluxed for 1 hour, diluted with water to about 150 ml. and filtered. The filtrate is treated with 2.5 ml. of acetic acid and 2-nitro-5-mercaptoaniline filtered off.

A solution of 3.4 g. of 2-nitro-5-mercaptoaniline in 20 ml. of dimethylformamide is treated with 0.5 g. of 100% sodium hydride. After 1 hour, 2.2 g. of chloromethyl ethyl ether is added. After a further hour, the solution is diluted with water and extracted with chloroform. Removal of the solvent leaves 2-nitro-5-(ethoxymethylthio)aniline.

In a similar manner, substituting chloromethyl methyl ether, chloroethyl methyl ether, chloroethyl ethyl ether, chloroethyl phenyl ether, 1-iodo-2,2,2-trifluoroethane, 2,2,3,3-tetrafluoro-1-iodopropane for the chloromethyl ethyl ether above, followed by reaction of the resultant compounds with methoxy carbonyl isothiocyanate, in similar manner to the procedure of the second paragraph of Example XXI affords: 1-(3-methoxycarbonyl-2-thioureido)-2-nitro-5-substituted benzenes where the substituent at the 5-position is ethoxymethylthio-, methoxymethylthio-, methoxyethylthio-, ethoxyethylthio-, phenoxyethylthio-, 2,2,2-trifluoroethylthio-, or 2,2,3,3-tetrafluoropropylthio-. The corresponding 1-(3-methoxycarbonyl-2-thioureido)-2-nitro-5-substitutedthiobenzenes can be reduced, according to the second paragraph of Example VII or the third paragraph of Example XXI, to afford the corresponding 2-amino derivatives, which, in turn, can be reacted with further methoxycarbonyl isothiocyanate to afford the 1,2-bis(3-methoxycarbonyl-2-thioureido)-4-substituted-thioderivatives, or they can be treated, according to the first paragraph of Example XXI, to afford the corresponding 5-substitutedsulfinyl derivatives which also can be reacted with further methoxycarbonyl isothiocyanate to afford the corresponding 1,2-bis(3-methoxycarbonyl-2-thioureido)-4-substituted-sulfinyl derivatives. The above reaction sequence through 1-nitro-2-amino-4-mercaptobenzene provides an additional route by which certain of the compounds of the invention can be prepared.

In the Examples above, specific reaction sequences have been extended, in a general sense, to the preparation of other similar and related compounds. It should be understood, however, that with respect to any compound which has been prepared by the extension of a specific reaction sequence, it may be necessary or desirable to utilize solvents, reaction media, trituration or recrystallization media, etc., other than the ones given in the specific reaction sequence upon which such extension is based. These variations are deemed to be within the skill of those working in this art and will be apparent from a consideration of the particular reactants utilized and/or particular compound desired to be produced.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound selected from the group of compounds represented by the formula:

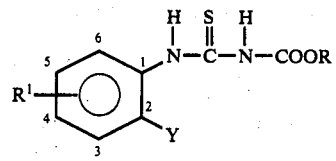

where R is a lower alkyl group having 1 to 4 carbon atoms; $R^1$ is $-SR^2$, $-SOR^2$, $-OR^2$, $-SCN$, or $-M'(CH_2)_nMR^7$ where n is 1-4; $R^2$ is lower alkyl having 1 to 6 carbon atoms, cycloalkyl having 3 to 7 carbon atoms, lower alkenyl or lower alkynyl having 3 to 6 carbon atoms, benzyl or phenyl, provided that when $R^1$ is $-SO_2R^2$, $R^2$ is not benzyl or phenyl, provided further that when $R^1$ is either $-SR^2$ or $-OR^2$, $R^2$ can not be either alkyl or cycloalkyl; Y is amino, nitro, alkanoylamino having 1 to 6 carbon atoms, $-NHC(O)(CH_2)_mCOOH$ where m is 1-6, or $-NHC(S)NHCOOR$; M and M' are independently O, S or

and $R^7$ is lower alkyl having 1 to 4 carbon atoms or phenyl; the $R^1$-substitution being at the 4- or 5-position; and the pharmaceutically acceptable salts thereof.

2. The compound of claim 1 wherein the $R^1$ substituent is at the 4-position.

3. The compound of claim 1 wherein the $R^1$ substituent is at the 5-position.

4. The compound of claim 1 wherein $R^1$ is $-SR^2$.

5. The compound of claim 1 wherein $R^1$ is $-SOR^2$.

6. The compound of claim 1 wherein $R^1$ is $-SO_2R^2$.

7. The compound of claim 1 wherein $R^1$ is $-OR^2$.

8. The compound of claim 1 wherein $R^1$ is $-SCN$.

9. The compound of claim 1 wherein $R^1$ is $-O(CH_2)_nOR^7$.

10. The compound of claim 1 wherein $R^1$ is $-O(CH_2)_nSR^7$.

11. The compound of claim 1 wherein $R^1$ is $-S(CH_2)_nOR^7$.

12. The compound of claim 1 wherein $R^2$ is lower alkyl.

13. The compound of claim 1 wherein $R^2$ is lower alkenyl.

14. The compound of claim 1 wherein $R^2$ is lower alkynyl.

15. The compound of claim 1 wherein $R^1$ is $-S(CH_2)_nSR^7$.

16. The compound of claim 1 wherein $R^2$ is benzyl.

17. The compound of claim 1 wherein $R^2$ is phenyl.

18. The compound of claim 1 wherein said compound is 2-amino-1-(3-methoxycarbonyl-2-thioureido)-4-(2-phenoxyethoxy)benzene.

19. The compound of claim 1 wherein 2-amino-1-(3-methoxycarbonyl-2-thioureido)-5-(2-phenoxyethoxy)-benzene.

20. The compound of claim 1 wherein Y is amino.

21. The compound of claim 1 wherein Y is nitro.

22. The compound of claim 1 wherein Y is acetamido.

23. The compound of claim 1 wherein Y is —NHC(S)NHCOOR.

24. The compound of claim 1 wherein Y is —NHC(S)NHCOOCH$_3$.

25. The compound of claim 1 wherein Y is —NHC(O)(CH$_2$)$_m$COOH.

26. The compound of claim 1 wherein R is methyl.

27. The compound of claim 1 wherein said compound is 2-amino-1-(3-methoxycarbonyl-2-thioureido)-4-methoxyethylsulfinylbenzene.

28. The compound of claim 1 wherein said compound is 2-amino-1-(3-methoxycarbonyl-2-thioureido)-5-methoxyethylsulfinylbenzene.

29. The compound of claim 1 wherein said compound is 1,2-bis-(3-methoxycarbonyl-2-thioureido)-4-methylsulfinylbenzene.

30. The compound of claim 1 wherein said compound is 1,2-bis-(3-methoxycarbonyl-2-thioureido)-4-thiocyanatobenzene.

31. The compound of claim 1 wherein said compound is 1,2-bis-(3-methoxycarbonyl-2-thioureido)-4-isopropylsulfinylbenzene.

32. The compound of claim 1 wherein said compound is 1,2-bis-(3-methoxycarbonyl-2-thioureido)-4-n-propylsulfinylbenzene.

33. The compound of claim 1 wherein said compound is 1,2-bis-(3-methoxycarbonyl-2-thioureido)-4-n-butylsulfinylbenzene.

34. The compound of claim 1 wherein said compound is 1,2-bis-(3-methoxycarbonyl-2-thioureido)-4-phenoxybenzene.

35. The compound of claim 1 wherein said compound is 1,2-bis-(3-methoxycarbonyl-2-thioureido)-4-ethylsulfinylbenzene.

36. The compound of claim 1 wherein said compound is 1,2-bis-(3-methoxycarbonyl-2-thioureido-4-methoxymethoxybenzene.

37. The compound of claim 1 wherein said compound is 1,2-bis-(3-methoxycarbonyl-2-thioureido)-4-ethoxymethoxybenzene.

38. The compound of claim 1 wherein said compound is 1,2-bis-(3-methoxycarbonyl-2-thioureido)-4-methoxymethylthiobenzene.

39. The compound of claim 1 wherein said compound is 1-(3-methoxycarbonyl-2-thioureido)-2-amino-4-methoxymethylsulfinylbenzene.

40. The compound of claim 1 wherein said compound is 1,2-bis-(3-methoxycarbonyl-2-thioureido)-4-methylthiomethoxybenzene.

41. The compound of claim 1 wherein said compound is 1-(3-methoxycarbonyl-2-thioureido)-2-amino-5-phenylsulfinylbenzene.

42. The compound of claim 1 wherein said compound is 1-(3-methoxycarbonyl-2-thioureido)-2-amino-4-phenylsulfinylbenzene.

43. The compound of claim 1 wherein said compound is 1-(3-methoxycarbonyl-2-thioureido)-2-amino-5-phenylthiobenzene.

44. The compound of claim 1 wherein said compound is 1-(3-methoxycarbonyl-2-thioureido-2-amino-4-phenylthiobenzene.

45. The compound of claim 1 wherein said compound is 2-acetamido-1-(3-methoxycarbonyl-2-thioureido)-5-benzylthiobenzene.

46. The compound of claim 1 wherein R$^1$ is $$-\underset{\underset{O}{\Downarrow}}{S}(CH_2)_nOR^7.$$

47. The compound of claim 1 wherein R$^1$ is $$-\underset{\underset{O}{\Downarrow}}{O}(CH_2)_nSR^7.$$

48. The compound of claim 1 wherein R$^7$ is phenyl.

49. The compound of claim 1 wherein R$^7$ is either methyl or ethyl.

50. The compound of claim 1 wherein said compound is 2-amino-1-(3-methoxycarbonyl-2-thioureido)-5-methoxymethylsulfinylbenzene.

51. 1,2-bis-(3-ethoxycarbonyl-2-thioureido)-4-phenylthiobenzene.

* * * * *